(12) United States Patent
Lee et al.

(10) Patent No.: US 9,956,244 B2
(45) Date of Patent: May 1, 2018

(54) BIOMARKER HSP90 FOR PREDICTING EFFECT OF A C-MET INHIBITOR

(71) Applicant: Samsung Electronics Co., Ltd., Suwon-si, Gyeonggi-do (KR)

(72) Inventors: Ji Min Lee, Seoul (KR); Bo Gyou Kim, Seoul (KR); Seung Ja Oh, Seoul (KR); Kyung Ah Kim, Seongnam-si (KR); Saet Byoul Lee, Seoul (KR); Jae Woong Hwang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 14/814,278

(22) Filed: Jul. 30, 2015

(65) Prior Publication Data
US 2016/0030559 A1 Feb. 4, 2016

(30) Foreign Application Priority Data
Jul. 30, 2014 (KR) .................. 10-2014-0097560

(51) Int. Cl.
| | | |
|---|---|---|
| *G01N 33/50* | (2006.01) | |
| *G01N 33/574* | (2006.01) | |
| *A61K 31/713* | (2006.01) | |
| *C07K 16/28* | (2006.01) | |
| *A61K 39/395* | (2006.01) | |
| *A61K 45/06* | (2006.01) | |
| *C07K 16/30* | (2006.01) | |

(52) U.S. Cl.
CPC ...... *A61K 31/713* (2013.01); *A61K 39/39533* (2013.01); *A61K 39/39558* (2013.01); *A61K 45/06* (2013.01); *C07K 16/2863* (2013.01); *C07K 16/30* (2013.01); *G01N 33/57484* (2013.01); *C07K 2317/24* (2013.01); *C07K 2317/31* (2013.01); *C07K 2317/52* (2013.01); *C07K 2317/54* (2013.01); *C07K 2317/565* (2013.01); *C07K 2317/622* (2013.01); *C07K 2317/76* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,984,389 B2 | 1/2006 | Li |
| 7,691,838 B2 | 4/2010 | Johnson, Jr. et al. |
| 8,029,808 B2 | 10/2011 | Srivastava |
| 8,563,696 B2 | 10/2013 | Cheong et al. |
| 8,591,890 B2 | 11/2013 | Srivastava et al. |
| 2011/0118298 A1 | 5/2011 | Fritz et al. |
| 2012/0064175 A1 | 3/2012 | Vukovic et al. |
| 2013/0023420 A1 | 1/2013 | Thomas et al. |
| 2015/0010575 A1* | 1/2015 | Kim ............... A61K 38/10 424/158.1 |
| 2015/0030599 A1* | 1/2015 | Cho ............... C07K 16/2863 424/136.1 |

FOREIGN PATENT DOCUMENTS

| | | |
|---|---|---|
| EP | 1572083 A2 | 9/2005 |
| EP | 1628667 A1 | 3/2006 |
| EP | 1631267 A2 | 3/2006 |
| EP | 2321645 A1 | 5/2011 |
| EP | 2499486 A1 | 9/2012 |
| EP | 2616063 A1 | 7/2013 |
| JP | 2006-501147 A | 1/2006 |
| JP | 2006-526644 A | 11/2006 |
| JP | 2012-500013 A | 1/2012 |
| JP | 2013-510585 A | 3/2013 |
| JP | 2013-537229 A | 9/2013 |
| KR | 2004-0106394 A | 12/2004 |
| KR | 2011-0047698 A | 5/2011 |
| WO | WO 2003/090686 A2 | 11/2003 |
| WO | WO 2005/000212 A2 | 1/2005 |
| WO | WO 2010/020618 A1 | 2/2010 |
| WO | WO 2011/060328 A1 | 5/2011 |
| WO | WO 2011/146803 A1 | 11/2011 |
| WO | WO 2012/037072 A1 | 3/2012 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Maulik et al., Clin Cancer Res., 2002, 8:620-627.*

* cited by examiner

*Primary Examiner* — Hong Sang
(74) *Attorney, Agent, or Firm* — Leydig, Voit & Mayer, Ltd.

(57) ABSTRACT

A biomarker Hsp90 for predicting an efficacy of a c-Met inhibitor, selecting a subject for application of a c-Met inhibitor, or monitoring an efficacy of a c-Met inhibitor, and a relevant method of using Hsp90.

6 Claims, 10 Drawing Sheets

SEQUENCE LISTING

```
<160> NUMBER OF SEQ ID NOS: 123

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46
```

```
<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
 1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
```

-continued

```
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
 1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46
```

```
<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone
```

```
<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
```

<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser

```
                    20                  25                  30
Gly Asn Gln Asn Asn Tyr Leu Ala Trp His Gln Gln Lys Pro Gly Lys
            35                  40                  45
Ala Pro Lys Met Leu Ile Ile Trp Ala Ser Thr Arg Val Ser Gly Val
    50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Ser Tyr Ser Arg Pro Phe Thr Phe Gly Gln Gly Thr Lys Val Glu Ile
            100                 105                 110
Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone
```

```
<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
 1               5                  10                  15

Ala

<210> SEQ ID NO 32
<211> LENGTH: 17
```

```
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
 1               5                  10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
 1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
 1               5
```

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
    chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg gttttattta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactggggc caagggactc tggtcactgt ctctgcagct     420
agcaccaagg gcccatcggt cttccccctg gcacctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200

```
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgcccct caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 40
<211> LENGTH: 447
<212> TYPE: PRT
<213> ORGANISM: Artificial Sequence
<220> FEATURE:

<223> OTHER INFORMATION: Synthetic amino acid sequence of H1-heavy

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Gln Lys Pro Gly Gln
         35                  40                  45

Pro Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
            35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
        210                 215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

| | | |
|---|---|---|
| gaggtgcagc tggtggagtc tggggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg gttgggcttt attagaaaca aagctaacgg ttacaccaca | 180 |
| gaatacagtg cgtctgtgaa aggcagattc accatctcaa gagataattc aaagaactca | 240 |
| ctgtatctgc aaatgaacag cctgaaaacc gaggacacgg ccgtgtatta ctgtgctaga | 300 |
| gataactggt ttgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc aaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

| | | |
|---|---|---|
| gaggtgcagc tggtggagtc tggggggaggc ttggtccagc ctggagggtc cctgagactc | 60 |
| tcctgtgcag cctctggatt caccttcact gactactaca tgagctgggt ccgccaggct | 120 |

```
ccagggaagg ggctggagtg gttgggcttt attagaaaca aagctaacgg ttacaccaca      180
gaatacagtg cgtctgtgaa aggcagattc accatctcaa gagataattc aaagaactca      240
ctgtatctgc aaatgaacag cctgcgtgct gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag       1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49
gaggttcagc tggtggagtc tggcggtggc ctggtgcagc caggggggctc actccgtttg      60 tcctgtgcag cttctggctt caccttcact gattactaca tgagctgggt gcgtcaggcc     120
ccgggtaagg gcctggaatg gttgggtttt attagaaaca agctaatgg ttacacaaca      180 gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
```

| | |
|---|---|
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

| | |
|---|---|
| gacatcgtga tgacccagtc tccagactcc ctggctgtgt ctctgggcga gagggccacc | 60 |
| atcaactgca gtccagcca gagtctttta gctagcggca accaaaataa ctacttagct | 120 |
| tggcaccagc agaaaccagg acagcctcct aagatgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

| | |
|---|---|
| gatattgtga tgacccagac tccactctcc ctgcccgtca cccctggaga gccggcctcc | 60 |
| atctcctgca agtccagtca gagtctttta gctagtggca ccaaaataa ctacttggcc | 120 |
| tggcacctgc agaagccagg gcagtctcca cagatgctga tcatttgggc atccactagg | 180 |
| gtatctggag tccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |

```
caatcgggta actcccagga gagtgtcaca gagcaggaca gcaaggacag caccttacagc    540 ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                             669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc     60
atcaactgca agtccagcca gagtctttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag caccctacagc    540 ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                             669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc     60
atcacctgca gtccagtca gagtctttta gctagtggca accaaaataa ctacttggcc    120
tggcaccaac agaaaccagg aaaagctccg aaaatgctga ttatttgggc atccactagg    180
gtatctggag tcccttctcg cttctctgga tccgggtctg gacggatttt cactctgacc    240
atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag caccctacagc    540 ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                             669
```

<210> SEQ ID NO 54

```
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga cacccttgta cttgcaaatg aactccttga gagctaaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc aatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gactttggt caaggtacaa aggtcgaaat caagagagaa     780
ttcggtaagc ctatccctaa ccctctcctc ggtctcgatt ctacgggtgg tgtggatct     840 ggtggtggtg gttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat acaaatcag taacgtttgt cagtaattgc    1020
ggttctcacc cctcaacaac tagcaaaggc agccccataa acacacagta tgttttttga    1080
gtttaaac                                                             1088

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
```

```
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactccct tgagagctga agatactgctg tttattactg cgctagagat aattggtttg     900
cttattgggg tcaaggtact ttggttactg tttcttctgg cctcggggc ctcggaggag     960 gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
```

```
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gtttttgaat   1560
attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg ttttcccatg taatatcctt ttctattttt     1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcattttga    2040 cgaaatttgc tattttgtta gagtcttta caccatttgt ctccacacct ccgcttacat    2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaagttca cctgtcccac ctgcttctga atcaaacaag ggaataaacg    2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat    2460 tacgaaacac gccaaccaag tatttcggag tgcctgaact attttatat gcttttacaa    2520 gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt cttttttcga ccgaatttct tgaagacgaa agggcctcgt    2820
gatacgccta ttttatagg ttaatgtcat gataataatg gtttcttagg acggatcgct    2880
tgcctgtaac ttacacgcgc ctcgtatctt ttaatgatgg aataatttgg gaatttactc   2940
tgtgtttatt tattttatg ttttgtattt ggattttaga aagtaaataa agaaggtaga    3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactattttt tctttaatt    3300 cttttttac tttctatttt taattatat atttatatta aaaatttaa attataatta     3360 tttttatagc acgtgatgaa aaggacccag gtggcacttt tcggggaaat gtgcgcggaa   3420
cccctatttg tttattttc taaatacatt caaatatgta tccgctcatg agacaataac    3480
cctgataaat gcttcaataa tattgaaaaa ggaagagtat gagtattcaa catttccgtg   3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
```

```
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960 ctttttttgca caacatgggg gatcatgtaa ctcgccttga tcgttgggaa ccggagctga    4020
atgaagccat accaaacgac gagcgtgaca ccacgatgcc tgtagcaatg caacaacgt     4080 tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc ctttttgata atctcatgac caaaatccct aacgtgagt     4500 tttcgttcca ctgagcgtca gaccccgtag aaaagatcaa aggatcttct tgagatcctt    4560 ttttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag cgcagcggt     4860 cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

```
<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtcagcagtc ctacagccgc ccgtacacgt tcggacaggg taccaaggtg   420
gagatcaaac gtacg                                                   435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtgggcagtc ctacagccgt ccgctcacgt tcggacaggg taccaaggtg   420
gagatcaaac gtacg                                                   435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtgcacagtc ctacagccat ccgttctctt tcggacaggg taccaaggtg   420
gagatcaaac gtacg                                                   435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
derived from L3-5 clone

<400> SEQUENCE: 61

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca gtccagtca gagtctttta      180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtttacgt tcggacaggg taccaaggtg     420
gagatcaaac gtacg                                                      435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
of huAbF46-H4-A1, U6-HC7 hinge and constant region of human IgG1

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
```

```
                210                 215                 220
Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt     180
caggccccgg gtaagggcct ggaatggttg gttttattga aaacaaagc taatggttac     240 acaacagagt acagtgcatc tgtgaagggt cgtttcacta agcagaga taattccaaa      300 aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcaccctcct ccaagagcac ctctggggc     480 acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
```

```
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG1

<400> SEQUENCE: 64

```
Met Glu Trp Ser Trp Val Phe Leu Val Thr Leu Leu Asn Gly Ile Gln
 1               5                  10                  15
Cys Glu Val Gln Leu Val Glu Ser Gly Gly Gly Leu Val Gln Pro Gly
            20                  25                  30
Gly Ser Leu Arg Leu Ser Cys Ala Ala Ser Gly Phe Thr Phe Thr Asp
        35                  40                  45
Tyr Tyr Met Ser Trp Val Arg Gln Ala Pro Gly Lys Gly Leu Glu Trp
    50                  55                  60
Leu Gly Phe Ile Arg Asn Lys Ala Asn Gly Tyr Thr Thr Glu Tyr Ser
65                  70                  75                  80
Ala Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Asp Asn Trp Phe Ala Tyr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
```

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa    300
aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600

```
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tggggggacc gtcagtcttc     780
ctcttccccc caaaacccaa ggacaccctc atgatctccc ggaccctga ggtcacatgc     840 gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg actcgag                                        1407

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG2

<400> SEQUENCE: 66

Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
             85                  90                  95

Thr Leu Tyr Leu Gln Met Asn Ser Leu Arg Ala Glu Asp Thr Ala Val
        100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205
```

```
Asn Phe Gly Thr Gln Thr Tyr Thr Cys Asn Val Asp His Lys Pro Ser
            210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
                275                 280                 285

Asn Trp Tyr Val Asp Gly Val Glu Val His Asn Ala Lys Thr Lys Pro
            290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactgggc caagggactc tggtcaccgt ctcctcggct    420
agcaccaagg gcccatcggt cttccccctg gcgccctgct ccaggagcac ctccgagagc    480
acagcggccc tgggctgcct ggtcaaggac tacttccccg aaccggtgac ggtgtcgtgg    540
```

```
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
of huAbF46-H4-A1(H36Y) and human kappa constant region

<400> SEQUENCE: 68

Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggg accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540 agtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                             758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

-continued

Lys Val Glu Ile Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

```
Tyr Met Ser Trp Val Arg Gln Ala Pro Gly Lys Gly Leu Glu Trp Leu
             35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
             85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Lys Pro Gly Gln
             35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
             85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
```

```
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag aaaggcact tgagtggttg gttttatta aaacaaagc taatggttac      240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc aagggactc tggtcactgt ctctgcagct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
```

<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

| | | | | | |
|---|---|---|---|---|---|
| gaattcacta | gtgattaatt | cgccgccacc | atggattcac | aggcccaggt | cctcatgttg | 60 |
| ctgctgctat | cggtatctgg | tacctgtgga | gacattttga | tgacccagtc | tccatcctcc | 120 |
| ctgactgtgt | cagcaggaga | gaaggtcact | atgagctgca | agtccagtca | gagtctttta | 180 |
| gctagtggca | accaaaataa | ctacttggcc | tggcaccagc | agaaaccagg | acgatctcct | 240 |
| aaaatgctga | taatttgggc | atccactagg | gtatctggag | tccctgatcg | cttcataggc | 300 |
| agtggatctg | ggacggattt | cactctgacc | atcaacagtg | tgcaggctga | agatctggct | 360 |
| gtttattact | gtcagcagtc | ctacagcgct | ccgctcacgt | tcggtgctgg | gaccaagctg | 420 |
| gagctgaaac | gtacggtggc | tgcaccatct | gtcttcatct | tcccgccatc | tgatgagcag | 480 |
| ttgaaatctg | gaactgcctc | tgttgtgtgc | ctgctgaata | acttctatcc | cagagaggcc | 540 |
| aaagtacagt | ggaaggtgga | taacgcccct | caatcgggta | actcccagga | gagtgtcaca | 600 |
| gagcaggaca | gcaaggacag | cacctacagc | ctcagcagca | ccctgacgct | gagcaaagca | 660 |
| gactacgaga | aacacaaagt | ctacgcctgc | gaagtcaccc | atcagggcct | gagctcgccc | 720 |
| gtcacaaaga | gcttcaacag | gggagagtgt | tgactcgag | | | 759 |

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

| | | | | | |
|---|---|---|---|---|---|
| atgaaggccc | ccgctgtgct | tgcacctggc | atcctcgtgc | tcctgtttac | cttggtgcag | 60 |
| aggagcaatg | gggagtgtaa | agaggcacta | gcaaagtccg | agatgaatgt | gaatatgaag | 120 |
| tatcagcttc | ccaacttcac | cgcggaaaca | cccatccaga | atgtcattct | acatgagcat | 180 |
| cacattttcc | ttggtgccac | taactacatt | tatgttttaa | atgaggaaga | ccttcagaag | 240 |
| gttgctgagt | acaagactgg | gcctgtgctg | gaacacccag | attgtttccc | atgtcaggac | 300 |
| tgcagcagca | aagccaattt | atcaggaggt | gtttggaaag | ataacatcaa | catggctcta | 360 |
| gttgtcgaca | cctactatga | tgatcaactc | attagctgtg | gcagcgtcaa | cagagggacc | 420 |
| tgccagcgac | atgtctttcc | ccacaatcat | actgctgaca | tacagtcgga | ggttcactgc | 480 |
| atattctccc | cacagataga | agagcccagc | cagtgtcctg | actgtgtggt | gagcgccctg | 540 |
| ggagccaaag | tccttttcatc | tgtaaaggac | cggttcatca | acttctttgt | aggcaatacc | 600 |
| ataaattctt | cttatttccc | agatcatcca | ttgcattcga | tatcagtgag | aaggctaaag | 660 |

```
gaaacgaaag atggttttat gttttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag aataatcagg    840 ttctgttcca taaactctgg attgcattcc tacatggaaa tgcctctgga gtgtattctc    900
acagaaaaga gaaaaagag atccacaaag aaggaagtgt ttaatatact tcaggctgcg    960
tatgtcagca agcctgggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg gacatggac tcaacagatc   1680 tgtctgcctg caatctacaa ggttttccca aatagtgcac cccttgaagg agggacaagg   1740
ctgaccatat gtggctggga ctttggattt cggaggaata taaatttga tttaaagaaa   1800 actagagttc tccttggaaa tgagagctgc accttgactt taagtgagag cacgatgaat   1860
acattgaaat gcagttggg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg agcacaata   2280 acaggtgttg ggaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc cctgaaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg tttttcctgt ggctgaaaaa gagaaagcaa   2880
attaaagatc tgggcagtga attagttcgc tacgatgcaa gagtacacac tcctcatttg   2940
gataggcttg taagtgcccg aagtgtaagc ccaactacag aaatggtttc aaatgaatct   3000
gtagactacc gagctacttt tccagaagat cagtttccta attcatctca gaacggttca   3060
```

```
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctactatgt gaacgtaaaa    4080
tgtgtcgctc cgtatccttc tctgttgtca tcagaagata acgctgatga tgaggtggac    4140
acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160
```

-continued

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
            195                 200                 205

Gln Arg Glu Thr Leu Asp Ala Gln Thr Phe His Thr Arg Ile Ile Arg
        210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
            290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
        370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

```
Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met
```

<400> SEQUENCE: 81

| | | | | | | | | | | |
|---|---|---|---|---|---|---|---|---|---|---|
|Val|His|Phe|Asn|Glu|Val|Ile|Gly|Arg|Gly|His|Phe|Gly|Cys|Val|Tyr
1| | | |5| | | | |10| | | | |15|

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180

```
aacatggctc tagttgtcga cacctactat gatgatcaac tcattagctg tggcagcgtc      240
aacagaggga cctgccagcg acatgtcttt ccccacaatc atactgctga catacagtcg      300
gaggttcact gcatattctc cccacagata gaagagccca gccagtgtcc tgactgtgtg      360
gtgagcgccc tgggagccaa agtcctttca tctgtaaagg accggttcat caacttcttt      420
gtaggcaata ccataaattc ttcttatttc ccagatcatc cattgcattc gatatcagtg      480
agaaggctaa aggaaacgaa agatgggtttt atgtttttga cggaccagtc ctacattgat      540
gttttacctg agttcagaga ttcttacccc attaagtatg tccatgcctt tgaaagcaac      600
aattttattt acttcttgac ggtccaaagg gaaactctag atgctcagac ttttcacaca      660
agaataatca ggttctgttc cataaactct ggattgcatt cctacatgga aatgcctctg      720
gagtgtattc tcacagaaaa gagaaaaaag agatccacaa agaaggaagt gtttaatata      780
cttcaggctg cgtatgtcag caagcctggg gcccagcttg ctagacaaat aggagccagc      840
ctgaatgatg acattctttt cggggtgttc gcacaaagca agccagattc tgccgaacca      900
atggatcgat ctgccatgtg tgcattccct atcaaatatg tcaacgactt cttcaacaag      960
atcgtcaaca aaaacaatgt gagatgtctc cagcattttt acggacccaa tcatgagcac      1020
tgctttaata ggacacttct gagaaattca tcaggctgtg aagcgcgccg tgatgaatat      1080
cgaacagagt ttaccacagc tttgcagcgc gttgacttat tcatgggtca attcagcgaa      1140
gtcctcttaa catctatatc caccttcatt aaaggagacc tcaccatagc taatcttggg      1200
acatcagagg gtcgcttcat gcaggttgtg gtttctcgat caggaccatc aacccctcat      1260
gtgaattttc tcctggactc ccatccagtg tctccagaag tgattgtgga gcatacatta      1320
aaccaaaatg gc                                                         1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg      120
tgccacgaca atgtgtgcg atcggaggaa tgcctgagcg ggacatggac tcaacagatc      180
tgtctgcctg caatctacaa ggttttccca atagtgcac cccttgaagg agggacaagg      240
ctgaccatat gtggctggga ctttggattt cggaggaata taaatttga tttaaagaaa      300 actagagttc tccttggaaa tgagagctgc accttgactt taagtgagag cacgatgaat      360
acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg aaaaacatg tactttaaaa      600 agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg agcacaata      780 acaggtgttg ggaaaaacct gaattcagtt agtgtcccga gaatggtcat aaatgtgcat      840
```

| | |
|---|---|
| gaagcaggaa ggaactttac agtggcatgt caacatcgct ctaattcaga gataatctgt | 900 |
| tgtaccactc cttccctgca acagctgaat ctgcaactcc ccctgaaaac caaagccttt | 960 |
| ttcatgttag atgggatcct ttccaaatac tttgatctca tttatgtaca taatcctgtg | 1020 |
| tttaagcctt tgaaaagcc agtgatgatc tcaatgggca atgaaaatgt actggaaatt | 1080 |
| aagggaaatg atattgaccc tgaagcagtt aaaggtgaag tgttaaaagt tggaaataag | 1140 |
| agctgtgaga atatacactt acattctgaa gccgttttat gcacggtccc caatgacctg | 1200 |
| ctgaaattga acagcgagct aaatatagag tggaagcaag caatttcttc aaccgtcctt | 1260 |
| ggaaaagtaa tagttcaacc agatcagaat ttcacagga | 1299 |

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

| | |
|---|---|
| gtgcatttca atgaagtcat aggaagaggg cattttggtt gtgtatatca tgggactttg | 60 |
| ttggacaatg atggcaagaa aattcactgt gctgtgaaat ccttgaacag aatcactgac | 120 |
| ataggagaag tttcccaatt tctgaccgag ggaatcatca tgaaagattt tagtcatccc | 180 |
| aatgtcctct cgctcctggg aatctgcctg cgaagtgaag gtctccgct ggtggtccta | 240 |
| ccatacatga acatggaga tcttcgaaat tcattcgaa atgagactca taatccaact | 300 |
| gtaaaagatc ttattggctt tggtcttcaa gtagccaaag catgaaaata tcttgcaagc | 360 |
| aaaaagtttg tccacagaga cttggctgca agaaactgta tgctggatga aaaattcaca | 420 |
| gtcaaggttg ctgattttgg tcttgccaga gacatgtatg ataaagaata ctatagtgta | 480 |
| cacaacaaaa caggtgcaaa gctgccagtg aagtggatgg cttggaaag tctgcaaact | 540 |
| caaaagttta ccaccaagtc agatgtgtgg tcctttggcg tgctcctctg ggagctgatg | 600 |
| acaagaggag ccccaccta tcctgacgta aacaccttg atataactgt tacttgttg | 660 |
| caagggagaa gactcctaca acccgaatac tgcccagacc ccttatatga agtaatgcta | 720 |
| aaatgctggc accctaaagc cgaaatgcgc ccatcctttt ctgaactggt gtcccgata | 780 |
| tcagcgatct tctctacttt cattggggag cactatgtcc atgtgaacgc tacttatgtg | 840 |
| aacgtaaaat gtgtcgctcc gtatccttct ctgttgtcat cagaagataa cgctgatgat | 900 |
| gaggtggaca cacgaccagc ctccttctgg agacatca | 939 |

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

Asp Asn Trp Phe Ala Tyr Trp Gly Gln Gly Thr Leu Val
 1               5                  10

<210> SEQ ID NO 86
<211> LENGTH: 10
<212> TYPE: PRT
<213> ORGANISM: Artificial Sequence

```
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
 65                 70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
 65                 70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg
```

```
<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110
```

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

```
Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110
```

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
           100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
 1               5                  10

<210> SEQ ID NO 103
<211> LENGTH: 14
<212> TYPE: PRT
<213> ORGANISM: Artificial Sequence

```
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
```

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
<223> OTHER INFORMATION: Synthetic CDR-H1 of anti-EGFR scFv

<400> SEQUENCE: 109

Asn Tyr Asp Met Ser
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic CDR-H2 of anti-EGFR scFv

<400> SEQUENCE: 110

```
Gly Ile Ser His Ser Ser Gly Ser Lys Tyr Tyr Ala Asp Ser Val Lys
  1               5                   10                  15

Gly

<210> SEQ ID NO 111
<211> LENGTH: 13
<212> TYPE: PRT
<213> ORGANISM: Artificial Sequence
<220> FEATURE:
<223> OTHER INFORMATION: Synthetic CDR-H3 of anti-EGFR scFv

<400> SEQUENCE: 111

Lys Asp Ala Thr Pro Arg Pro Leu Lys Pro Phe Asp Tyr
  1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic CDR-L1 of anti-EGFR scFv

<400> SEQUENCE: 112

Thr Gly Ser Ser Ser Asn Ile Gly Asn Asn Asp Val Ser
  1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic CDR-L2 of anti-EGFR scFv

<400> SEQUENCE: 113

Asp Asp Asn Lys Arg Pro Ser
  1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic CDR-L3 of anti-EGFR scFv

<400> SEQUENCE: 114

Gly Ser Trp Asp Ala Ser Leu Asn Ala
  1               5

<210> SEQ ID NO 115
<211> LENGTH: 121
<212> TYPE: PRT
<213> ORGANISM: Artificial Sequence
<220> FEATURE:
<223> OTHER INFORMATION: Synthetic Heavy chain variable region of
      anti-EGFR scFv

<400> SEQUENCE: 115

Glu Val Gln Leu Leu Glu Ser Gly Gly Gly Leu Val Gln Pro Gly Gly
  1               5                   10                  15

Ser Leu Arg Leu Ser Cys Ala Ala Ser Gly Phe Thr Phe Ser Asn Tyr
             20                  25                  30

Asp Met Ser Trp Val Arg Gln Ala Pro Gly Lys Gly Leu Glu Trp Val
         35                  40                  45

Ser Gly Ile Ser His Ser Ser Gly Ser Lys Tyr Tyr Ala Asp Ser Val
```

```
                    50                    55                     60

Lys Gly Arg Phe Thr Ile Ser Arg Asp Asn Ser Lys Asn Thr Leu Tyr
 65                  70                 75                  80

Leu Gln Met Asn Ser Leu Arg Ala Glu Asp Thr Ala Val Tyr Tyr Cys
                 85                  90                  95

Ala Lys Asp Ala Thr Pro Arg Pro Leu Lys Pro Phe Asp Tyr Trp Gly
              100                 105                 110

Gln Gly Thr Leu Val Thr Val Ser Ser
          115                 120

<210> SEQ ID NO 116
<211> LENGTH: 111
<212> TYPE: PRT
<213> ORGANISM: Artificial Sequence
<220> FEATURE:
<223> OTHER INFORMATION: Synthetic Light chain variable region of
      anti-EGFR scFv

<400> SEQUENCE: 116

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
                 20                  25                  30

Asp Val Ser Trp Tyr Gln Gln Leu Pro Gly Thr Ala Pro Lys Leu Leu
             35                  40                  45

Ile Tyr Asp Asp Asn Lys Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Asn Ala Tyr Val Phe Gly Gly Gly Thr Lys Leu Thr Val Leu Gly
             100                 105                 110

<210> SEQ ID NO 117
<211> LENGTH: 121
<212> TYPE: PRT
<213> ORGANISM: Artificial Sequence
<220> FEATURE:
<223> OTHER INFORMATION: Synthetic heavy chain variable region of
      anti-EGFR antibody (modified)

<400> SEQUENCE: 117

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Asp Met Ser Trp Val Arg Gln Ala Pro Gly Lys Cys Leu Glu Trp Val
             35                  40                  45

Ser Gly Ile Ser His Ser Gly Ser Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Thr Pro Arg Pro Leu Lys Pro Phe Asp Tyr Trp Gly
             100                 105                 110

Gln Gly Thr Leu Val Thr Val Ser Ser
```

115                 120

<210> SEQ ID NO 118
<211> LENGTH: 111
<212> TYPE: PRT
<213> ORGANISM: Artificial Sequence
<220> FEATURE:
<223> OTHER INFORMATION: Synthetic light chain variable region of
      anti-EGFR antibody (modified)

<400> SEQUENCE: 118

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Cys Gly Thr Lys Leu Thr Val Leu Gly
            100                 105                 110

<210> SEQ ID NO 119
<211> LENGTH: 363
<212> TYPE: DNA
<213> ORGANISM: Artificial Sequence
<220> FEATURE:
<223> OTHER INFORMATION: Synthetic coding nucleotide sequence of heavy
      chain variable region of anti-EGFR antibody

<400> SEQUENCE: 119
gaggtgcagc tgttggagtc tgggggaggc ttggtacagc ctggggggtc cctgagactc      60
tcctgtgcag cctctggatt caccttagc aattatgata tgagctgggt ccgccaggct     120
ccagggaagg ggctggagtg ggtctcaggg atctctcata gtagtggtag taaatattac     180
gctgattctg taaaaggtcg gttcaccatc tccagagaca attccaagaa cacgctgtat     240
ctgcaaatga acagcctgag agccgaggac acggccgtgt attactgtgc gaaagatgct     300
actccgcgtc cgctgaagcc tttcgactac tggggccagg gtacactggt caccgtgagc     360
tca                                                                  363

<210> SEQ ID NO 120
<211> LENGTH: 333
<212> TYPE: DNA
<213> ORGANISM: Artificial Sequence
<220> FEATURE:
<223> OTHER INFORMATION: Synthetic coding nucleotide sequence of light
      chain variable region of anti-EGFR antibody

<400> SEQUENCE: 120
cagtctgtgc tgactcagcc accctcagcg tctgggaccc ccgggcagag ggtcaccatc      60
tcttgtactg gctcttcatc taatattggc aataatgatg tctcctggta ccagcagctc     120
ccaggaacgg ccccccaaact cctcatctat gatgataata gcggccaag cggggtccct      180 gaccgattct ctggctccaa atctggcacc tcagcctccc tggccatcag tgggctccgg     240
tccgaggatg aggctgatta ttactgtggt tcttgggatg ctagcctgaa tgcttatgtc     300
ttcggcggag gcaccaagct gacggtccta ggc 333

<210> SEQ ID NO 121
<211> LENGTH: 114
<212> TYPE: PRT
<213> ORGANISM: Artificial Sequence
<220> FEATURE:
<223> OTHER INFORMATION: Synthetic light chain variable region of anti
       c-Met antibody

<400> SEQUENCE: 121

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 122
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(55)
<223> OTHER INFORMATION: Xaa can be any naturally occurring amino acid
<220> FEATURE:
<221> NAME/KEY: MISC_FEATURE
<222> LOCATION: (6)..(55)
<223> OTHER INFORMATION: Sequence can be repeated up to 10 times

<400> SEQUENCE: 122

Gly Gly Gly Gly Ser Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa
        50                  55

<210> SEQ ID NO 123
<211> LENGTH: 15
<212> TYPE: PRT
<213> ORGANISM: Artificial Sequence
<220> FEATURE:
<223> OTHER INFORMATION: Synthetic

```
<400> SEQUENCE: 123

Gly Gly Gly Gly Ser Gly Gly Gly Gly Ser Gly Gly Gly Gly Ser
1               5                   10                  15
```

BIOMARKER HSP90 FOR PREDICTING EFFECT OF A C-MET INHIBITOR

CROSS-REFERENCE TO RELATED APPLICATIONS

This application claims the benefit of Korean Patent Application No. 10-2014-0097560 filed on Jul. 30, 2014 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 140,376 byte ASCII (Text) file named "721060_ST25-Revised.TXT," created Jan. 9, 2017.

BACKGROUND OF THE INVENTION

1. Field

Provided herein are methods of predicting an effect of a c-Met inhibitor or selecting a subject for application of a c-Met inhibitor. The methods comprise measuring Hsp90 protein levels and/or expression levels of an Hsp90 coding gene. Further provided are methods of monitoring an effect of a c-Met inhibitor comprising measuring Hsp90 protein levels and/or expression levels of an Hsp90 coding gene. Also provided are methods of decreasing a resistance to a c-Met inhibitor comprising administering an Hsp90 inhibitor to a subject and methods of treating and/or preventing cancer comprising co-administering an Hsp90 inhibitor and a c-Met inhibitor to a subject.

2. Description of the Related Art

The term "biomarker" generally refers to a measured characteristic which may be used as an indicator of some change caused in an organism by an external factor. Active studies have recently been made to apply biomarkers to the diagnosis of various diseases, such as cancer, stroke, dementia, etc., and to the prediction or monitoring of therapeutic effects of some agents. Among biomarkers relevant to drug development are pharmacodynamic markers (PD markers) for indicating whether drugs are functionally effective in vivo, and predictive markers for indicating the most likely response to particular drugs before administration. The use of such markers is helpful in establishing the clinical strategy of drugs. For example, a predictive marker, designed to indicate sensitivity or resistance to drug action, may be applied to the selection of patients to allow for more effective drug therapy while the action mode of a drug in individual patients can be monitored with a pharmacodynamic marker, which together can lead to the establishment of effective therapeutic strategies. Further, even in the absence of a predictive marker, a pharmacodynamic marker permits the early monitoring of responses to a drug, thus discriminating a drug-effective group from a drug-ineffective group in an early stage. Consequentially, more effective and successful drug therapies can be materialized. In addition, when applied to the monitoring of responses to a drug as a function of concentrations, a pharmacodynamic marker can be an index for calculating suitable doses of the drug.

Cancer is one of the leading causes of death. Although the development of medical techniques has brought about a remarkable progress in cancer therapy, the 5-year survival rate has only improved by 10% over the past two decades. This is because cancer characteristics, such as rapid growth, metastasis, etc., make it difficult to diagnose and treat within a suitable time. The introduction of suitable biomarkers to cancer therapy would identify the characteristics of cancer to increase the opportunity of applying a suitable therapeutic in an optimal time, whereby cancer treatment could reach high success rates. For example, patients with lung cancer may differ from each other in cancer classification, genotype, and protein secretion, and thus must be treated with different, proper therapeutics. For chemotherapy using a specific drug, a corresponding biomarker, if present, would reduce the number of erroneous trials and increase possibility of success. In this regard, it is very important to explore biomarkers for predicting or monitoring the effect of anti-cancer therapeutics. A proper biomarker, if successfully exploited, can make a great contribution to the utility and value of anti-cancer drugs and the success rate of treatment with them.

c-Met is a receptor for hepatocyte growth factor (HGF) that possesses tyrosine kinase activity. Hepatocyte growth factor acts as a multi-functional cytokine which binds to the extracellular domain of the c-Met receptor to regulate cell division, cell motility, and morphogenesis in various normal and tumor cells. c-Met is a proto-oncogene that takes part in a variety of mechanisms responsible for the development of cancer independent of HGF binding, such as oncogenesis, cancer metastasis, the migration and invasion of cancer cells, and angiogenesis. Thus, c-Met has attracted intensive attention as a target for anti-cancer therapy. For example, targeted therapies, such as antibodies against c-Met, have been developed.

c-Met-targeting drugs might be more effective at treating cancer if there is a biomarker that is useful in predicting and monitoring the therapeutic effect of the drug, or in selecting patients suitable for the drug therapy and thereafter monitoring patient responses to the drug.

There is a need for biomarkers useful for predicting the effect of the c-Met targeting drugs to select a subject who is suitable for application of the c-Met targeting drugs, and/or for monitoring the responsiveness of a patient who has been treated with the c-Met targeting drugs to establish more effective treatment strategies using the c-Met targeting drugs.

BRIEF SUMMARY OF THE INVENTION

Provided herein is a method of predicting an efficacy of a c-Met inhibitor or selecting a subject for application of a c-Met inhibitor, wherein the method includes measuring Hsp90 protein level and/or Hsp90 gene expression level; detecting a mutation of Hsp90 and/or an Hsp90 coding gene; or detecting dysfunction of Hsp90 protein in a biological sample from a patient; and determining that the c-Met inhibitor is capable of exerting an effect in the biological sample, or selecting the patient for application of the c-Met inhibitor, when the Hsp90 protein level or the Hsp90 gene expression level in the biological sample from the patient is lower than that of a reference sample in which the c-Met inhibitor has no effect, a mutation of Hsp90 or an Hsp90 coding gene is identified in the biological sample, and/or dysfunction of Hsp90 is identified in the biological sample.

Another embodiment provides a method for monitoring efficacy of a c-Met inhibitor in a subject, including measuring the presence and/or the level (or the amount or the concentration) of Hsp90 protein or the expression level of an Hsp90 coding gene in a c-Met inhibitor-treated biological sample, and determining that the c-Met inhibitor is effective in the biological sample or a patient from whom the biological sample is isolated when the Hsp90 protein level and/or Hsp90 gene expression level in the c-Met inhibitor-treated biological sample is lower than that of c-Met inhibitor-untreated biological sample.

Another embodiment provides a method of enhancing an efficacy a c-Met inhibitor or decreasing a resistance to a c-Met inhibitor in a subject with a cancer resistant to treatment with a c-Met inhibitor, including administering an Hsp90 inhibitor to the subject.

Another embodiment provides a pharmaceutical composition for treating and/or preventing a cancer, including a c-Met inhibitor and an Hsp90 inhibitor. The cancer may be resistant to a c-Met inhibitor.

Another embodiment provides a method of treating and/or preventing a cancer in a subject, including co-administering a c-Met inhibitor and an Hsp90 inhibitor to the subject. The cancer may be resistant to a c-Met inhibitor.

DETAILED DESCRIPTION OF THE INVENTION

Figure 1:
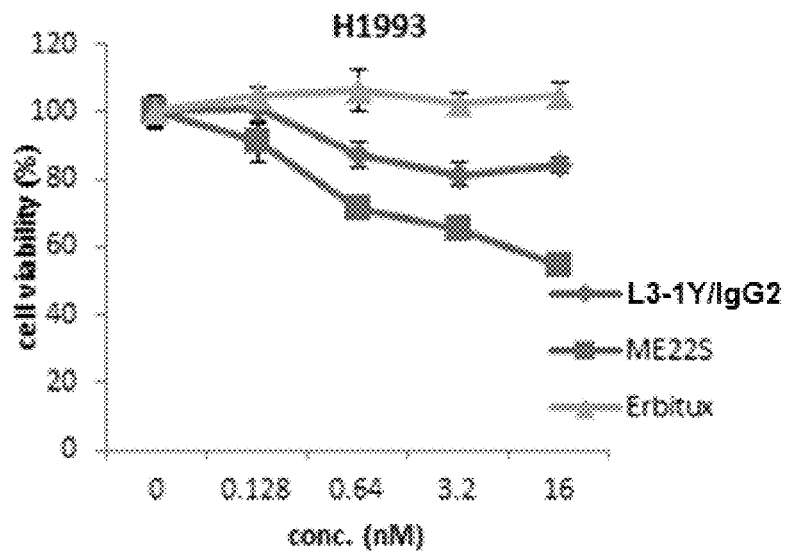
FIG. 1 provides graphs displaying the degree of cell proliferation (cell viability (%)) in an anti-c-Met antibody responder group (H1993 lung cancer cell line, top panel) or an anti-c-Met antibody non-responder group (H1373 lung cancer cell line, bottom panel) treated with anti-c-Met antibody L3-1Y/IgG2, anti-c-Met/anti-EGFR bispecific antibody ME22S, or Erbitux.
Figure 1:
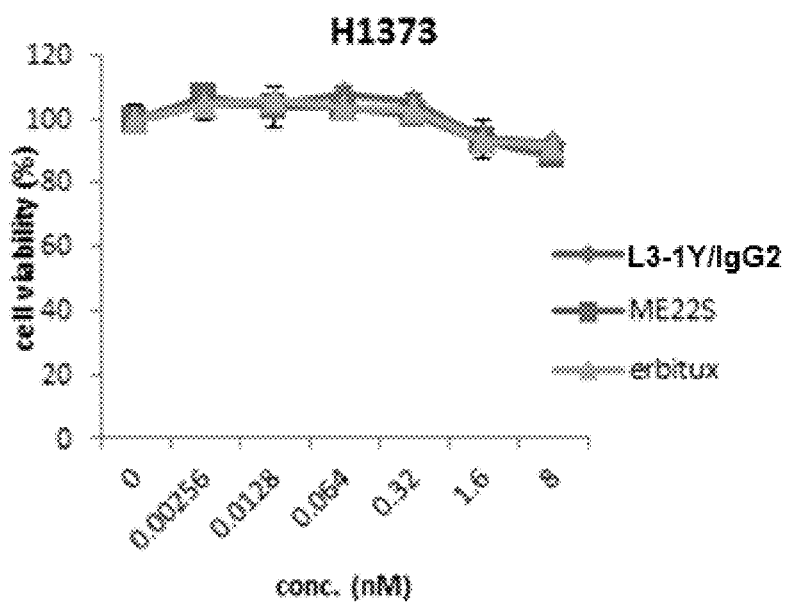

Provided herein are methods for predicting efficacy of a c-Met inhibitor and/or monitoring whether or not a resistance to a c-Met inhibitor is induced in a patient having been administered the c-Met inhibitor; selecting a patient for treatment with a c-Met inhibitor; and treating a c-Met inhibitor resistant cancer. The c-Met inhibitor may refer to a composition or a compound, which targets c-Met and is useful for preventing, improving, alleviating, and/or treating a c-Met associated disease, such as a cancer. For example, c-Met-inhibitor treatment may cause an inhibition of c-Met signaling, a decrease in cancer cells or cancer tissues, death of cancer cells or cancer tissues, an inhibition of cancer cell migration and/or invasion associated with cancer metastasis, and the like.

Hsp90 (heat shock protein 90) is a chaperone protein, and is known to play an important role in stabilizing proteins which are necessary in tumor growth. Hsp90 assists other proteins (client proteins) to fold properly, stabilizes proteins against heat stress, and aids in protein degradation. It also stabilizes a number of proteins required for tumor growth, relating to cancer incidence or cancer growth. The term "90" refers that the molecular weight of Hsp90 is about 90 kDa. Hsp90 is expressed in all eukaryotes, such as yeast and mammals, including rodents (e.g., a mouse, a rat, etc.), primates (a human, a monkey, etc.), and the like. The following are examples of known Hsp90 sequences: yeast Hps90 (e.g., NCBI Accession No. NP_013911.1, NP_015084.1, etc.), human Hsp90 (e.g., NCBI Accession No. NP_001017963.2, NP_005339.3, etc.), mouse Hsp90 (e.g., NCBI Accession No. NP_034610.1, NP_032328.2, etc.), rat Hsp90 (e.g., NCBI Accession No. NP_786937.1, AAT99569.1, etc.), and the like. Hsp90 coding gene (e.g., mRNA) may be at least one selected from the group consisting of yeast Hsp90 (e.g., NCBI Accession No. NM_001182692.1, NM_001184054.1, etc.), human Hsp90 (e.g., NCBI Accession No. NM_001017963.2, NM_005348.3, etc.), mouse Hsp90 (e.g., NCBI Accession No. NM_010480.5, NM_008302.3, etc.), rat Hsp90 (e.g., NCBI Accession No. NM_175761.2, AY695393.1, etc.), and the like.

Without wishing to be bound by any particular theory or mechanism of action, it is believed that responsiveness to a c-Met inhibitor depends on the level and/or mutation and/or dysfunction of Hsp90, and acquisition of a resistance to a c-Met inhibitor after c-Met inhibitor treatment is related to functional Hsp90 levels. When the level of Hsp90 protein or Hsp90 coding gene in a biological sample is low, a c-Met inhibitor exhibits an effect on the biological sample or a patient from who the biological sample is isolated. When a biological sample exhibits innate or acquired resistance to a c-Met inhibitor (e.g., an anti-c-Met antibody), induced by treating the sample with the c-Met inhibitor (e.g., an anti-c-Met antibody) once or more, the level of Hsp90 or Hsp90 coding gene is relatively high or becomes increased in response to treatment with the c-Met inhibitor. When Hsp90 or an Hsp90 coding gene has a mutation (e.g., A577N (yeast Hsp90), A577D (yeast Hsp90), C598A (human Hsp90), etc.) and/or a dysfunction (e.g., dysfunction of Hsp90 ATPase, etc.), a c-Met inhibitor exhibits higher efficacy or induces no or low c-Met-inhibitor resistance, compared to with a biological sample having no mutation and/or dysfunction.

Thus, measurement of the expression level and/or mutation and/or dysfunction of Hsp90 or an Hsp90 coding gene in a biological sample is useful for predicting efficacy of a c-Met inhibitor on the biological sample or a patient from who the biological sample is isolated and for selecting a subject who is suitable for application of the c-Met inhibitor. In addition, measurement of the expression level and/or mutation and/or dysfunction of Hsp90 or an Hsp90 coding gene in c-Met-inhibitor-treated and non-treated biological samples is also useful for monitoring acquisition of resistance to the c-Met inhibitor, monitoring efficacy of the c-Met inhibitor in the biological sample, and in determining whether the treatment of the c-Met inhibitor can be continued or not. Therefore, provided herein are methods for using Hsp90 as a biomarker for predicting and/or monitoring an efficacy of a c-Met inhibitor.

c-Met inhibitor treatment dissociates the binding between Hsp90 and c-Met, thereby exhibiting therapeutic effects on c-Met-associated disease. However, when the level of Hsp90 is high, a c-Met inhibitor cannot exhibit its effect. Therefore, Hsp90 is useful for predicting efficacy of a c-Met inhibitor. In addition, when resistance to a c-Met inhibitor is induced by long term or repeated exposure to the c-Met inhibitor, Hsp90 expression level increases, and/or a mutation in the Hsp90 amino acid sequence and/or a dysfunction of Hsp90 is observed. Therefore, by measuring the Hsp90 expression level (amount), a presence of a mutation in the Hsp90 amino acid sequence or gene encoding the amino acid sequence, and/or a presence of a dysfunction of Hsp90 prior to applying a c-Met inhibitor, a patient having an innate resistance to a c-Met antibody can be detected. In addition, by measuring and comparing the level of Hsp90 before and after applying a c-Met inhibitor, or identifying the presence of mutation or dysfunction of Hsp90 after applying a c-Met inhibitor, acquisition of resistance to the c-Met inhibitor can be monitored. In addition, when the acquired or innate resistance to a c-Met inhibitor is caused by quantitative increase of Hsp90, the resistance can be overcome by co-administering a c-Met inhibitor with an agent to decrease the level of Hsp90 or inhibit the function of Hsp90.

An embodiment provides a biomarker for predicting an efficacy of a c-Met inhibitor and/or selecting a subject for applying a c-Met inhibitor, comprising Hsp90, Hsp90 coding gene, or a combination thereof.

Another embodiment provides a biomarker for monitoring an efficacy of a c-Met inhibitor in a subject who is treated with the c-Met inhibitor, comprising Hsp90, Hsp90 coding gene, or a combination thereof.

An embodiment provides a composition for predicting an efficacy of a c-Met inhibitor and/or selecting a subject for applying a c-Met inhibitor, comprising a substance interacting with Hsp90, Hsp90 coding gene, modified Hsp90, modified Hsp90 coding gene, or a combination thereof.

Another embodiment provides a kit for predicting an efficacy of a c-Met inhibitor and/or selecting a subject for applying a c-Met inhibitor, comprising a substance interacting with Hsp90, Hsp90 coding gene, modified Hsp90, modified Hsp90 coding gene, or a combination thereof and a means detecting the interacting between the substance and Hsp90.

Another embodiment provides a composition and a kit for monitoring an efficacy of a c-Met inhibitor in a subject who is treated with the c-Met inhibitor, comprising a substance interacting with Hsp90, Hsp90 coding gene, modified Hsp90, modified Hsp90 coding gene, or a combination thereof.

Another embodiment provides a kit for monitoring an efficacy of a c-Met inhibitor in a subject who is treated with the c-Met inhibitor, comprising a substance interacting with Hsp90, Hsp90 coding gene, modified Hsp90, modified Hsp90 coding gene, or a combination thereof and a means detecting the interacting between the substance and Hsp90.

Another embodiment provides a method for predicting or monitoring an efficacy of a c-Met inhibitor and/or selecting a subject for applying a c-Met inhibitor, comprising measuring the level of Hsp90; detecting a mutation of Hsp90 or an Hsp90 coding gene, measuring Hsp90 gene expression levels, detecting dysfunction of Hsp90, or combination thereof, in a biological sample.

As used herein, the term "predicting an efficacy of a c-Met inhibitor" may refer to predicting whether or not a c-Met inhibitor can exhibit a desired effect on a patient to be treated with the c-Met inhibitor by measuring and/or identifying a condition or a factor affecting the c-Met inhibitor to exhibit its desired effect, such as presence or absence of an innate resistance to the c-Met inhibitor. The term "monitoring an efficacy of a c-Met inhibitor" may refer to monitoring whether or not the c-Met inhibitor exhibits a desired effect in a c-Met inhibitor treated subject, and/or whether or not a resistance to the c-Met inhibitor is induced by administration of the c-Met inhibitor. As used in the description, the "efficacy" or "effect" of a c-Met inhibitor refers to the anti-cancer effect (e.g., inhibition of cancer cell proliferation, etc.), anti-migration effect, anti-invasion effect, anti-metastasis effect, and/or c-Met signaling inhibition effect of the c-Met inhibitor, particularly anti-cancer effect, anti-migration effect, and/or anti-invasion effect of the c-Met inhibitor, unless stated otherwise.

In an embodiment, a method for predicting an efficacy of a c-Met inhibitor and/or selecting a subject for applying a c-Met inhibitor, comprising measuring Hsp90 level; detecting a mutation of Hsp90 or an Hsp90 coding gene, measuring Hsp90 gene expression level; and/or detecting a dysfunction of Hsp90, in a biological sample. The level of an Hsp90 coding gene, also referred to as Hsp90 gene expression level, can be determined by any suitable method, such as by measuring mRNA levels.

As described above, a high level of Hsp90 protein and/or Hsp90 coding gene expression in a biological sample may indicate that the biological sample or a patient from which the biological sample is isolated has a resistance to a c-Met inhibitor. Therefore, in the method for predicting an efficacy of a c-Met inhibitor or selecting a subject for applying a c-Met inhibitor, when the level of Hsp90 protein and/or Hsp90 coding gene expression is low, it can be determined that a c-Met inhibitor can exhibit an effect in the biological sample or a patient from which the biological sample is isolated, or the biological sample or a patient from which the biological sample is isolated can be determined as a subject suitable for applying a c-Met inhibitor. Thus, the method for predicting an efficacy of a c-Met inhibitor may further comprise determining (or predicting) that a c-Met inhibitor exhibits an effect on the biological sample or a patient from which the biological sample is isolated, when the level of at least one selected from the group consisting of Hsp90 and Hsp90 coding genes is low. In addition, the method for selecting a subject for applying a c-Met inhibitor may further comprise determining (or considering) the biological sample or a patient from which the biological sample is isolated as a subject suitable for applying a c-Met inhibitor, when the level of at least one selected from the group consisting of Hsp90 and Hsp90 coding genes is low.

A biological sample from a patient is said to have a "low level of Hsp90 protein and/or Hsp90 coding gene" when Hsp90 protein and/or Hsp90 coding gene is absent, or the amount of Hsp90 protein and/or Hsp90 coding gene (DNA, cDNA, or mRNA) in the biological sample from the patient is lower than that in a reference sample. The reference sample may comprise a biological sample on which a c-Met inhibitor, such as an anti-c-Met antibody, has no effect or which has a resistance to a c-Met inhibitor. For example, the reference sample may be at least one selected from the group consisting of cell lines H1373 (ATCC, CRL-5866), HCC1806 (ATCC, CRL-2335), Caki-1 (ATCC, HTB-46), SKBR3 (ATCC, HTB-30), BT474 (ATCC, HTB-20), HT-29 (ATCC, HTB-38), LoVo (ATCC, CCL-229), HCT116 (ATCC, CCL-247), SW620 (ATCC, CCL-227), Ls174T (ATCC, CL-188), and c-Met-inhibitor-resistant cells (e.g., cells acquiring a resistance to a c-Met inhibitor by repeated and/or consistent administration of the c-Met inhibitor). In this case, the method for predicting an efficacy of a c-Met inhibitor and/or selecting a subject for applying a c-Met inhibitor may further comprise measuring the level of Hsp90; detecting a mutation of Hsp90 or an Hsp90 coding gene, measuring Hsp90 gene expression levels, detecting dysfunction of Hsp90, or combination thereof, in the reference sample, before the determining step. In addition, the method for predicting an efficacy of a c-Met inhibitor and/or selecting a subject for applying a c-Met inhibitor may further comprise comparing the level of Hsp90 and/or Hsp90 gene of the biological sample to that of the reference sample.

Alternatively, the level of Hsp90 may be determined by immunohistochemical staining using a general antibody (e.g., Cell signaling, #4874) against Hsp90. Methods of immunohistochemical staining are routine among persons of ordinary skill in the art. Immunohistochemical staining is a method for identifying a material present in a cell or a tissue using antigen-antibody response, wherein a frozen or paraffin tissue section is generally used. A tissue section having a regular thickness is blocked for preventing non-specific binding of an antibody and then treated with a primary antibody. After a certain period, non-reacting primary antibody is removed, and the tissue section is treated with a secondary antibody. The secondary antibody can be detected using a streptavidin-coupled material, such as streptavidin-HRP or streptavidin-alkaline phosphatase, which can bind to biotin coupled to the secondary antibody. Most of the detecting responses are color reactions, which can be analyzed by a proper microscope. The staining may be scored on a scale ranging, e.g., '−', '0', '+1', '+2' or '+3,' wherein a score (stain intensity) of '−' or '0' represents no protein expression (no signal, negative), a score of '+1' represents no or a slight protein expression (corresponding to a background signal), and scores of '+2' (strongly positive) to '+3' (very strongly positive) represent progressively increasing levels of protein expression (the case showing the signal higher than '+3' is incorporated in the score of '+3') (the scores can be determined by a pathologist). Thus, when the score measured by immunohistochemical staining is "−", "0", or "+1", the level of Hsp90 may be determined as "negative", and when the score measured by immunohistochemical staining is greater than "+1" (i.e., "+2", or "+3"), the level of Hsp90 may be determined as "positive", where the "negative" may be understood as absence, or presence at a low level, of Hsp90 in the biological sample. Therefore, when the score measured by immunohistochemical staining using an antibody (e.g., Cell signaling, #4874) against Hsp90 is "−", "0", or "+1", it can be determined that "the level of Hsp90 protein and/or Hsp90 coding gene is low".

In another embodiment, when a mutation of Hsp90 and/or Hsp90 coding gene, and/or dysfunction of Hsp90 is detected (or identified) in a biological sample, it can be determined (or predicted) that a c-Met inhibitor exerts an effect on the biological sample or a patient from which the biological sample is isolated, or that the biological sample or the patient has no or low resistance to a c-Met inhibitor, compared to a biological sample with no mutation of Hsp90 and/or Hsp90 coding gene, and/or dysfunction of Hsp90. Therefore, provided are methods for predicting an efficacy of a c-Met inhibitor further comprising determining (or predicting) that a c-Met inhibitor exhibits an effect on a biological sample or a patient from which the biological sample is isolated, when a mutation of Hsp90 and/or Hsp90 coding genes and/or dysfunction of Hsp90 is detected (or identified) in the biological sample. In addition, provided are methods for selecting a subject for application of a c-Met inhibitor comprising determining (or considering) if a biological sample or a patient from which the biological sample is isolated is suitable for application of a c-Met inhibitor, when a mutation of Hsp90 and/or Hsp90 coding gene, and/or dysfunction of Hsp90 is detected (or identified) in the biological sample.

The mutation of Hsp90 may refer to a mutation wherein at least one amino acid of an amino acid sequence of Hsp90 is deleted or substituted with another amino acid. The mutation of Hsp90 gene may refer to a mutation in a genomic DNA, cDNA or mRNA encoding Hsp90 resulting in deletion or substitution of at least one amino acid. For example, the mutation of Hsp90 may be a deletion of an amino acid residue at position 598 of human Hsp90 (e.g., NCBI Accession No. NP_005339.3; in this case, the amino acid residue at position 598 is Cys) or at a corresponding position of a Hsp90 other than human Hsp90. A position corresponding to position 598 of human Hsp90 may be determined by general sequence alignment between an amino acid sequences of human Hsp90 and other Hsp90 of interest. For example, yeast Hsp90 (NCBI Accession No. NP_015084.1) comprises Ala at position 577, which corresponds to position 598 of human Hsp90. The mutation of Hsp90 may be at least one selected from the group consisting of:

i) a substitution of the Cys residue at position 598 of human Hsp90 (NCBI Accession No. NP_005339.3) with Ala (C598A), ii) a substitution of the Ala residue at position 577 of yeast Hsp90 (NCBI Accession No. NP_015084.1) with Asn (A577N) or Asp (A577D), iii) a mutation in Hsp90 from species other than human and yeast, which mutation corresponds to the substitution of Cys at the position 598 of human Hsp90 with Ala (C598A) or Ala at the position 598 of yeast Hsp90 with Asn (A577N) or Asp (A577D), and iv) a mutation in Hsp90 genomic DNA, cDNA or mRNA comprising the mutation i), ii), or iii).

In addition, the dysfunction of Hsp90 can be identified by detecting the presence of a mutation (e.g., substitution) at the $128^{th}$ position of human Hsp90 alpha (NCBI Accession No. NP_005339.3). For example, the amino acid residue at human Hsp90 (NCBI Accession No. NP_005339.3), isoleucine (I), can be substituted with threonine (T) (I128T mutation). When such mutation is detected (or present), the dysfunction of Hsp90 can be identified.

The mutation of Hsp90 or Hsp90 genes can be identified (or detected) by any general method for analyzing an amino acid sequence of a protein or a nucleotide sequence of a gene. For example, the mutation of Hsp90 or Hsp90 genes can be identified (or detected) using a substance interacting with the mutated Hsp90 or the gene encoding the mutated Hsp90. For example, the substance interacting with the mutated Hsp90 or the gene encoding the mutated Hsp90 may be at least one selected from the group consisting of chemicals (small molecular agent), antibodies, and aptamers, which interacts with the mutated Hsp90, and primers, probes, and aptamers, which are capable of hybridizing with the gene encoding the mutated Hsp90.

The mutation of Hsp90 and/or Hsp90 coding gene may be identified (or detected) using by any general means for a gene or protein analysis assay. For example, the mutation of Hsp90 and/or Hsp90 coding gene may be identified (or detected) via an ordinary enzyme reaction, fluorescence, luminescence, and/or radioactivity detection using at least one selected from the group consisting of Hsp90 specific antibodies, and aptamers. More particularly, it may be identified (or detected) by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, polymerase chain reaction (PCR; e.g., qPCR), FISH (fluorescent in situ hybridization), microarray, and the like, but not be limited thereto.

The primer may be able to detect a gene fragment (comprising the mutated site) of about 5 to about 1000 bp, about 10 to about 500 bp, about 20 to about 200 bp, or about 50 to about 200 bp within the nucleotide sequence of a Hsp90 coding gene (full-length DNA, cDNA, or mRNA), and it may a primer pair each of which comprises or consists essentially of a nucleotide sequence hybridizable with (e.g., complementary to) a region of about 5 to about 100 bp, about 5 to about 50 bp, about 5 to about 30 bp, or about 10 to about 25 bp of the 3'-end and/or 5'-end of the gene fragment.

The probe or aptamer capable of hybridizing with the gene may comprise or consist essentially of a nucleotide sequence (comprising the mutated site) with a size from about 5 to about 100 bp, from about 5 to about 50 bp, from about 5 to about 30 bp, or from about 5 to about 25 bp, which is capable of hybridizing with (e.g., complementary to) a fragment (about 5 to about 100 bp, about 5 to about 50 bp, about 5 to about 30 bp, or about 5 to about 25 bp) of Hsp90 coding gene (full-length DNA, cDNA or mRNA). As used herein, the term "capable of hybridizing with" or "hybridizable with" may refer to that the primer, probe or aptamer has a sequence complementarity of 80% or higher, e.g., 90% or higher, 95% or higher, 98% or higher, 99% or higher, or 100%, with a specific region of a gene, thereby capable of complementarily binding to the specific region of the gene.

In the present disclosure, the mutation may a mutation leading to a dysfunction of Hsp90, for example, a dysfunction of ATPase function. The a dysfunction of Hsp90, for example, a dysfunction of ATPase function, may be caused by the mutation of Hsp90 or Hsp90 coding gene, as described above (e.g. C598A or I128T in human Hsp90 or A577N or A577D in yeast Hsp90), In an embodiment, a method for monitoring an efficacy of a c-Met inhibitor in a subject, comprising measuring the level and/or mutation of at least one selected from the group consisting of Hsp90 and Hsp90 coding gene, and/or a dysfunction of Hsp90, in a biological sample from the subject. As described above, the method for monitoring an efficacy of a c-Met inhibitor in a subject may comprise a monitoring whether or not the subject who is treated with a c-Met inhibitor acquires a resistance to the c-Met inhibitor.

In the method for monitoring an efficacy of a c-Met inhibitor, the level of Hsp90 protein and/or Hsp90 coding gene in a c-Met inhibitor-treated biological sample and a c-Met inhibitor-untreated biological sample may be measured respectively and compared to each other. When the level of Hsp90 protein and/or Hsp90 coding gene in a c-Met inhibitor-treated biological sample is decreased or maintained compared to that of a c-Met inhibitor-untreated biological sample, it can be determined that the c-Met inhibitor exerts a desired effect in the biological sample or the subject who is treated with the c-Met inhibitor. In addition, when the level of Hsp90 protein and/or Hsp90 coding gene in a c-Met inhibitor-treated biological sample is increased compared to that of a c-Met inhibitor-untreated biological sample, it can be determined that a resistance to the c-Met inhibitor is induced in the biological sample or the subject who is treated with the c-Met inhibitor.

Therefore, the method for monitoring an efficacy of a c-Met inhibitor comprises: measuring the level of Hsp90 protein and/or Hsp90 coding gene in both a c-Met-inhibitor-treated biological sample and a c-Met-inhibitor-untreated biological sample. In addition, the method for monitoring an efficacy of a c-Met inhibitor further comprises:

comparing Hsp90 protein level and/or Hsp90 gene expression level in a c-Met-inhibitor-treated biological sample and c-Met-inhibitor-untreated biological sample; and/or determining that (a) the c-Met inhibitor exerts a desired effect in the biological sample or the subject after being treated (or administered) with the c-Met inhibitor, when the level of Hsp90 protein and/or Hsp90 gene expression in a c-Met inhibitor-treated biological sample is decreased or maintained compared to that of a c-Met inhibitor-untreated biological sample, and/or (b) a resistance to the c-Met inhibitor is induced in the biological sample or the subject who is treated with the c-Met inhibitor c-Met inhibitor, when the level of Hsp90 and/or Hsp90 coding gene in a c-Met inhibitor-treated biological sample is increased compared to that of a c-Met inhibitor-untreated biological sample. The c-Met inhibitor may be an anti-c-Met antibody.

In this disclosure, the term "c-Met inhibitor-treated biological sample" may refer to a biological sample isolated from a subject after the subject is treated with a c-Met inhibitor, or a biological sample, which is treated with a c-Met inhibitor after being isolated from the subject. The term "c-Met inhibitor-untreated biological sample" may refer to a biological sample isolated from a subject before the subject is treated with a c-Met inhibitor, or a biological sample isolated from a subject, which is not treated with a c-Met inhibitor (i.e., treated with a vehicle only) after being isolated from the subject. In the disclosure, the term "c-Met inhibitor-treated biological sample" may by synonymous with "a post-treatment biological sample", and the term "c-Met inhibitor-untreated biological sample" may by synonymous with "a pre-treatment biological sample."

The method for monitoring an efficacy of a c-Met inhibitor may be useful in determining whether to continue administration of the c-Met inhibitor, and/or in determining suitable dosing conditions (e.g., dose, dosing interval, number of doses, etc.) of the c-Met inhibitor. It may be determined that administration of the c-Met inhibitor can be continued when the Hsp90 protein level and/or Hsp90 gene expression level in the c-Met inhibitor-treated biological sample is decreased compared to the c-Met inhibitor-untreated biological sample. For example, when the Hsp90 protein level and/or Hsp90 gene expression level in the c-Met inhibitor-treated biological sample is about 0 to about 80%, about 0 to about 70%, about 0 to about 60%, about 0 to about 50%, about 0 to about 40%, about 0 to about 30%, about 0 to about 20%, or about 0 to about 10% of that of the c-Met inhibitor-untreated biological sample, it may be determined that administration of the c-Met inhibitor can be continued.

The dosing condition of the c-Met inhibitor may be determined to be suitable when the Hsp90 protein level and/or Hsp90 gene expression level in the c-Met inhibitor-treated biological sample is decreased compared to the c-Met inhibitor-untreated biological sample, for example, when the level of Hsp90 and Hsp90 coding gene in the c-Met inhibitor-treated biological sample is about 0 to about 80%, about 0 to about 70%, about 0 to about 60%, about 0 to about 50%, about 0 to about 40%, about 0 to about 30%, about 0 to about 20%, or about 0 to about 10% of that of the c-Met inhibitor-untreated biological sample. The dosing condition may be at least one selected from the group consisting of a dose, a dosing interval, a number of doses, and the like.

In the method of predicting an efficacy of a c-Met inhibitor, selecting a subject for applying a c-Met inhibitor, or monitoring an efficacy of a c-Met inhibitor, the measuring of the Hsp90 protein level and/or Hsp90 gene expression level in a biological sample may comprise i) applying (adding) to the biological sample a substance interacting with Hsp90 and/or Hsp90 coding gene; and ii) quantitatively analyzing the resulting reaction mixture to determine the Hsp90 protein level and/or Hsp90 gene expression level. In an embodiment, prior to the step i), a step of preparing a biological sample may be further performed, wherein the preparation step may comprise obtaining (isolating) a biological sample from the patient or obtaining a biological sample which has been isolated from a patient. In step i), the interacting substance, as described above, may be at least one selected from the group consisting of a chemical (small molecule), an antibody, an aptamer, all binding to Hsp90, and a polynucleotide (e.g., a primer, a probe, an aptamer) binding to a part or entirety of a gene encoding Hsp90, and optionally, may be conjugated with a label, such as a fluorophore or a dye. The step i) may be configured to form a complex by applying (adding) the interacting substance to the biological sample. In step ii), the reaction mixture may be a complex resulting from interaction (binding) between at least one selected from the group consisting of Hsp90 and Hsp90 coding gene and the interacting substance, which can be obtained in step i). The quantitatively analyzing step may comprise quantifying the complex, the marker conjugated to the complex, or Hsp90 and/or Hsp90 coding gene segregated from the complex after the isolation of the complex from the biological sample. The quantitative analysis of Hsp90 may be performed by any general quantifying means of proteins, such as ELISA, immunohistochemistry, and the like, and the quantitative analysis of Hsp90 coding gene may be performed by any general quantifying means of genes (DNA or RNA), such as qPCR, mRNA microarray, and the like, but not limited thereto. Methods for quantifying protein levels and gene expression levels are routine for persons of ordinary skill in the art.

The level of Hsp90 and/or Hsp90 coding gene may be measured using any ordinary means for a gene or protein quantitative assay using a substance interacting with Hsp90 and/or Hsp90 coding gene. For example, the substance interacting with Hsp90 and/or Hsp90 coding gene may be at least one selected from the group consisting of chemicals (small molecules), proteins, peptides, nucleic acids (polynucleotides, oligonucleotides, etc.), and the like, which are specifically interact with (or bind to) Hsp90 and/or Hsp90 coding gene. For example, the substance interacting with Hsp90 and/or Hsp90 coding gene may be at least one selected from the group consisting of chemicals, antibodies, and aptamers, which specifically bind to Hsp90, and nucleic acids (e.g., primers, probes, aptamers, etc.) which bind to a whole or a part (e.g., about 5 to about 100 bp, about 5 to about 50 bp, about 5 to about 30 bp, or about 5 to about 25 bp) of Hsp90 coding gene.

For example, the level of Hsp90 may be measured via an ordinary enzyme reaction, fluorescence, luminescence, and/or radioactivity detection using at least one selected from the group consisting of Hsp90 specific antibodies, and aptamers. More particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, and the like, but is not limited thereto.

In addition, the level of Hsp90 coding gene (full-length DNA, cDNA, or mRNA) may be measured by using any ordinary gene quantification methods comprising, but not limited to, an ordinary polymerase chain reaction (PCR; e.g., qPCR, qRT(reverse transcription)-PCR), FISH (fluorescent in situ hybridization), microarray, and the like, using a primer, probe, or aptamer, which is hybridizable with the gene. For example, the expression level of Hsp90 coding gene can be measured by measuring the level of Hsp90 mRNA e.g., using qRT-PCR. Methods for determining gene expression level in biological samples are routine for persons of ordinary skill in the art.

The primer may be able to detect a gene fragment of about 5 to about 1000 bp, about 10 to about 500 bp, about 20 to about 200 bp, or about 50 to about 200 bp within the nucleotide sequence of a Hsp90 coding gene (full-length DNA, cDNA, or mRNA), and it may a primer pair each of which comprises or consists essentially of a nucleotide sequence hybridizable with (e.g., complementary to) a region of about 5 to about 100 bp, about 5 to about 50 bp, about 5 to about 30 bp, or about 5 to about 25 bp of the 3'-end and/or 5'-end of the gene fragment.

The probe or aptamer capable of hybridizing with the gene may comprise a nucleotide sequence with a size from about 5 to about 100 bp, from about 5 to about 50 bp, from about 5 to about 30 bp, or from about 5 to about 25 bp, which is capable of hybridizing with (e.g., complementary to) a fragment (about 5 to about 100 bp, about 5 to about 50 bp, about 5 to about 30 bp, or about 5 to about 25 bp) of Hsp90 coding gene (full-length DNA, cDNA or mRNA). As used herein, the term "capable of hybridizing with" or "hybridizable with" may refer to a primer, probe or aptamer having a sequence complementarity of 80% or higher, e.g., 90% or higher, 95% or higher, 98% or higher, 99% or higher, or 100%, with a specific region of a gene, thereby being capable of complementarily binding to the specific region of the gene.

From the point of view of using a c-Met inhibitor such as an anti-c-Met antibody, at least a certain expression level of c-Met in cancer cells is prerequisite for a c-Met inhibitor therapy (so that the c-Met inhibitor can exhibit its desired effect in the administered subject). Therefore, c-Met and/or c-Met coding gene can be also used as a marker for predicting an efficacy of a c-Met inhibitor, selecting a subject for applying a c-Met inhibitor, and/or monitoring an efficacy of a c-Met inhibitor, solely or in combination with Hsp90 and/or Hsp90 coding gene.

Accordingly, the composition and/or kit for predicting an efficacy of a c-Met inhibitor, selecting a subject for applying a c-Met inhibitor, or monitoring an efficacy of a c-Met inhibitor may further comprise a substance interacting with at least one selected from the group consisting of c-Met and c-Met coding gene, in addition to a substance interacting with at least one selected from the group consisting of Hsp90 and Hsp90 coding gene. The interacting substance with c-Met and/or c-Met coding gene may be at least one selected from the group consisting of chemicals (small molecules), proteins, peptides, nucleic acids (polynucleotides, oligonucleotides, etc.), and the like, which specifically interact with (or bind to) c-Met and/or c-Met coding gene. For example, the substance interacting with c-Met and/or c-Met coding gene may be at least one selected from the group consisting of chemicals, antibodies, and aptamers, which specifically bind to c-Met, and nucleic acids (e.g., primers, probes, aptamers, etc.) which bind to an whole or a part (e.g., about 5 to about 100 bp, about 5 to about 50 bp, about 5 to about 30 bp, or about 5 to about 25 bp) of c-Met coding gene, which may be labeled with a general labeling material, such as a fluorophore, a coloring material, and the like.

In addition, the method for predicting an efficacy of a c-Met inhibitor, selecting a subject for applying a c-Met inhibitor, or monitoring an efficacy of a c-Met inhibitor may further comprise measuring a level of c-Met protein or a gene thereof (e.g., full-length DNA, cDNA, mRNA) in the biological sample from the subject. The steps of measuring the level of c-Met and/or c-Met coding gene and measuring the level of Hsp90 and/or Hsp90 coding gene may be performed simultaneously or sequentially in any order. Details of the measuring step are as described above. For example, a western blotting technique may be employed. In this regard, when a predetermined amount (e.g., about 10 μg) of proteins obtained from a biological sample (e.g., cancer cells or cancer tissues) is loaded and exposed on the membrane for a certain time (e.g., about 30 sec), the detection of a band may indicate that a prerequisite for the c-Met inhibitor therapy is established. In another embodiment, when a biological sample is found to have a relative c-Met mRNA level of about 13.5 or higher, about 13.6 or higher, or about 13.78 or higher, as measured by Affymetrix array wherein the normal, non-cancer control sample c-Met mRNA level is normalized to a value of 1 (e.g., Affymetrix U133 Plus 2.0 array), a prerequisite for the c-Met inhibitor therapy may be established. Cancer cells characterized by a high expression level of c-Met comprise cells from lung cancer, breast cancer, brain cancer, stomach cancer, liver cancer, and kidney cancer. However, any cancer cell, although derived from different kinds, may be a target of the c-Met inhibitor therapy if it expresses a high level of c-Met.

In another embodiment, a biological sample used in the method for predicting an efficacy of a c-Met inhibitor or selecting a subject suitable to the application of a c-Met inhibitor may be a tissue, a cell, body fluid (blood, serum, urine, saliva, etc.), or a combination thereof, which shows a high expression level of c-Met, for example, a c-Met level of about 13.5 or higher, about 13.6 or higher, or about 13.78 or higher, as measured by Affymetrix array.

As used herein, the term "subject for the applying a c-Met inhibitor" or "a c-Met inhibitor-applicable subject" may refer to a patient to which a c-Met inhibitor therapy is suitable, and may be one selected from the group consisting of mammals, rodents, mice, rats, primates, humans, monkeys, etc. The patient may be a cancer patient. The biological sample may be the patient itself (mammals, such as primates, e.g., humans, monkeys, etc., or rodents, e.g., mice, rats, etc.) or a cell, a tissue, or body fluid (e.g., blood, serum, urine, saliva, etc.) isolated from the patient. For example, the biological sample may be blood or a serum.

In an embodiment, the predicting, monitoring, or selecting method may further comprise administering the c-Met inhibitor to the patient or subject who is determined to be responsive to the c-Met inhibitor, to maintain the responsiveness to the c-Met inhibitor after administration, or to be suitable for application of the c-Met inhibitor, e.g., after determining step.

Another embodiment provides a method for inhibiting c-Met, comprising administering a c-Met inhibitor to the selected subject for applying a c-Met inhibitor.

Another embodiment provides a method for preventing and/or treating a cancer, comprising administering a c-Met inhibitor to the selected subject for applying a c-Met inhibitor.

The method for inhibiting c-Met or the method for preventing and/treating cancer may further comprise selecting a subject for applying a c-Met inhibitor, prior to the administering step. Details of the selection are as described above. The c-Met inhibitor may be an anti-c-Met antibody.

In an embodiment, the method for inhibiting c-Met or for preventing and/or treating cancer may comprise:
identifying (or selecting) a subject for applying a c-Met inhibitor; and
administering a c-Met inhibitor to the subject, for example, at a pharmaceutically effective amount.

In another embodiment, the method for inhibiting c-Met or for preventing and/or treating cancer may comprise:
measuring the level of Hsp90 and/or Hsp90 coding gene in a biological sample, to select a c-Met inhibitor-applicable subject; and
administering a c-Met inhibitor to the selected c-Met inhibitor-applicable subject, for example, at a pharmaceutically effective amount.

The dosing conditions (e.g., dose, dosing interval, number of doses, etc.) of the c-Met inhibitor may be conditions selected by the method of monitoring an efficacy of a c-Met inhibitor, as described above.

In a therapy using a c-Met inhibitor, when Hsp90 and/or Hsp90 gene is inhibited, a c-Met inhibitor can recover its anticancer effect even in a c-Met inhibitor resistant cancer cell. In addition, when both of c-Met and Hsp90 are inhibited, an anticancer effect of a c-Met inhibitor, in particular, on in a c-Met inhibitor resistant cancer cell is considerably improved compared to the case where only c-Met is inhibited. Therefore, the co-administration of a c-Met inhibitor with an inhibitor against Hsp90 and/or Hsp90 coding gene may lead to a synergistic effect.

Therefore, another embodiment provides a pharmaceutical composition for decreasing a resistance to a c-Met inhibitor, comprising an inhibitor against Hsp90 and/or Hsp90 coding gene, as an active ingredient. Another embodiment provides a pharmaceutical composition for preventing and/or treating a cancer, comprising an inhibitor against Hsp90 and/or Hsp90 coding gene, as an active ingredient. Another embodiment provides a method of decreasing a resistance to a c-Met inhibitor, comprising administering an inhibitor against Hsp90 and/or Hsp90 coding gene to a subject in need of decreasing a resistance to a c-Met inhibitor. Another embodiment provides a method of preventing and/or treating a cancer in a subject, comprising administering an inhibitor against Hsp90 and/or Hsp90 coding gene, to the subject. The cancer may be a c-Met inhibitor resistant cancer. In the method, the inhibitor against Hsp90 and/or Hsp90 coding gene may be administered at pharmaceutically effective amounts for exerting a desired effect.

Another embodiment provides a pharmaceutical composition for combination administration for decreasing a resistance to a c-Met inhibitor, comprising a c-Met inhibitor and an inhibitor against Hsp90 and/or Hsp90 coding gene, as active ingredients. Another embodiment provides a pharmaceutical composition for combination administration for preventing and/or treating a cancer, comprising a c-Met inhibitor and an inhibitor against Hsp90 and/or Hsp90 coding gene, as active ingredients.

In one embodiment, the pharmaceutical composition for combination administration may be in a form for simultaneous administration of two agents comprising a mixture of a pharmaceutically effective amount of a c-Met inhibitor and a pharmaceutically effective amount of an inhibitor against Hsp90 and/or Hsp90 coding gene. In another embodiment, the pharmaceutical composition for combination administration may be in a form of simultaneous or sequential administration of a pharmaceutically effective amount of a c-Met inhibitor and a pharmaceutically effective amount of an inhibitor against Hsp90 and/or Hsp90 coding gene, each being individually formulated. In this case, the pharmaceutical composition for combination administration may be a pharmaceutical composition for combination administration for simultaneous or sequential administration comprising a first pharmaceutical composition containing a pharmaceutically effective amount of a c-Met inhibitor and a second pharmaceutical composition containing a pharmaceutically effective amount of an inhibitor against Hsp90 and/or Hsp90 coding gene. In the case of sequential administration, it can be performed in any order.

Another embodiment provides a kit for preventing and/or treating cancer or decreasing a resistance to a c-Met inhibitor, comprising a first pharmaceutical composition containing a pharmaceutically effective amount of a c-Met inhibitor, a second pharmaceutical composition containing a pharmaceutically effective amount of an inhibitor against Hsp90 and/or Hsp90 coding gene, and a package container.

Another embodiment provides a method of decreasing a resistance to a c-Met inhibitor in a subject, comprising co-administering a c-Met inhibitor and an inhibitor against Hsp90 and/or Hsp90 coding gene to the subject. Another embodiment provides a method of preventing and/or treating a cancer in a subject, comprising co-administering a c-Met inhibitor and an inhibitor against Hsp90 and/or Hsp90 coding gene, to the subject. The cancer may be a c-Met inhibitor resistant cancer. In the method, the c-Met inhibitor and the inhibitor against Hsp90 and/or Hsp90 coding gene may be administered at pharmaceutically effective amounts for exerting a desired effect. The method may further comprise identifying a subject in need of decreasing a resistance to a c-Met inhibitor or preventing and/or treating a cancer, prior to the administering step.

The co-administration (combination administration) step may be performed either by administering a c-Met inhibitor and an inhibitor against Hsp90 and/or Hsp90 coding gene together (at the same time) or by administering them sequentially in any order. In one embodiment, the combination administration may be performed by administering a mixture of a pharmaceutically effective amount of a c-Met inhibitor and a pharmaceutically effective amount of an inhibitor against Hsp90 and/or Hsp90 coding gene. In another embodiment, the combination administration may be done by performing a first step of administering a pharmaceutically effective amount of a c-Met inhibitor and a second step of administering a pharmaceutically effective amount of an inhibitor against Hsp90 and/or Hsp90 coding gene simultaneously or sequentially. In the case of sequential administration, it can be performed in any order.

The subject may be mammals such as primates, comprising humans and monkeys, and rodents, comprising mice and rats, or cells or tissues isolated from the living body thereof.

Another embodiment provides a Hsp90 mutant (or mutated Hsp90) as described above, or a polynucleotide encoding the same. The Hsp90 mutant or a polynucleotide encoding the same may be used as a marker for predicting an efficacy of a c-Met inhibitor, selecting a subject for applying a c-Met inhibitor, or monitoring an efficacy of a c-Met inhibitor, for example an anti-c-Met antibody. The Hsp90 mutant may contain deletion and/or substitution in at least one amino acid causing a dysfunction of Hsp90, for example, a dysfunction as an ATPase. For example, the Hsp90 mutant may contain a deletion of an amino acid residue at position 598 of human Hsp90 (e.g., NCBI Accession No. NP_005339.3; in this case, the amino acid residue at position 598 is Cys) or an amino acid residue at a corresponding position of a Hsp90 other than human Hsp90. The corresponding position refers to a position determined by general sequence alignment between an amino acid sequences of human Hsp90 and other Hsp90 of interest. For example, yeast Hsp90 (NCBI Accession No. NP_015084.1) comprises Ala at position 577, which corresponds to position 598 of human Hsp90. The mutation of Hsp90 gene may be a mutation in genomic DNA, cDNA or mRNA encoding the mutated Hsp90 (having such deletion or substitution of an amino acid residue at position 598 of human Hsp90 or at corresponding position of a Hsp90 other than human Hsp90).

The Hsp90 mutant may contain at least one mutation selected from the group consisting of:

i) a substitution of the Cys residue at position 598 of human Hsp90 (NCBI Accession No. NP_005339.3) with Ala (C598A), ii) a substitution of the Ala residue at position 577 of yeast Hsp90 (NCBI Accession No. NP_015084.1) with Asn (A577N) or Asp (A577D), iii) a mutation of Hsp90 other than human Hsp90 and yeast Hsp90, which corresponds to the substitution of Cys at the position 598 of human Hsp90 with Ala (C598A) or Ala at the position 598 of yeast Hsp90 with Asn (A577N) or Asp (A577D), and iv) a mutation in a genomic DNA, cDNA or mRNA encoding the mutated Hsp90 having the mutation i), ii), or iii).

Another embodiment provides a composition for predicting an efficacy of a c-Met inhibitor, selecting a subject for applying a c-Met inhibitor, or monitoring an efficacy of a c-Met inhibitor, for example an anti-c-Met antibody, comprising a substance interacting with at least one selected from the group consisting of the Hsp90 mutant and a gene encoding the same. The interacting substance is as described above.

In a particular embodiment, the Hsp90 inhibitor (referring to an inhibitor against Hsp90 and/or Hsp90 coding gene) may comprise any substance capable of inhibiting an expression and/or a function of Hsp90 and/or Hsp90 coding gene. For example, the Hsp90 inhibitor may be at least one selected from the group consisting of antibodies, aptamers, and chemicals (small molecular compounds and pharmaceutically acceptable salts thereof), which specifically recognize and/or bind to Hsp90, nucleic acids (e.g., aptamers, antisense oligonucleotides, siRNA (small interfering RNA), shRNA (small hairpin RNA), miRNA (microRNA), etc.) specifically binding (or having complementary sequence) to a whole or a part (e.g., about 5 to about 100 bp, about 5 to about 50 bp, about 5 to about 30 bp, or about 5 to about 25 bp) of Hsp90 coding gene, or a combination thereof. For example, the Hsp90 inhibitor may be at least one selected from the group consisting of anti-Hsp90 antibodies, siRNA against Hsp90 gene, SNX-2112 (PF-04928473; see the following chemical formula), geldanamycin, 17-AAG (17-(Allylamino)-17-desmethoxygeldanamycin), and the like, but not be limited thereto.

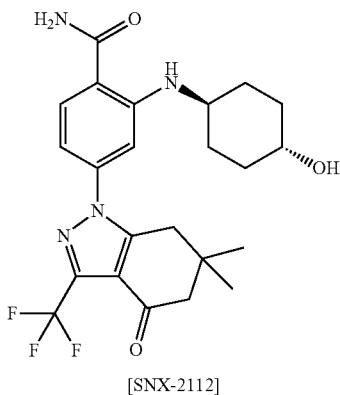

[SNX-2112]

The c-Met inhibitor may be any substance capable of inhibiting an expression and/or a function of c-Met protein and/or c-Met coding gene. For example, the c-Met inhibitor may be at least one selected from the group consisting of antibodies, aptamers, and chemicals (small molecular compounds and pharmaceutically acceptable salts thereof), which specifically recognize and/or bind to c-Met, nucleic acids (e.g., aptamers, antisense oligonucleotides, siRNA (small interfering RNA), shRNA (small hairpin RNA), miRNA (microRNA), etc.) specifically binding (or having complementary sequence) to a whole or a part (e.g., about 5 to about 100 bp, about 5 to about 50 bp, about 5 to about 30 bp, or about 5 to about 25 bp) of c-Met coding gene, or a combination thereof. For example, the c-Met inhibitor may be at least one selected from the group consisting of an anti-c-Met antibody or an antigen-binding fragment thereof, crizotinib (PF-02341066; 3-((R)-1-(2,6-dichloro-3-fluorophenyl)ethoxy)-5-(1-(piperidin-4-yl)-1H-pyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxy)quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), SU11274((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio)quinoline), PF-04217903 (2-(4-(3-(quinolin-6-ylmethyl)-3H-[1,2,3]triazolo[4,5-b]pyrazin-5-yl)-1H-pyrazol-1-yl)ethanol), EMD 1214063(Benzonitrile, 3-[1,6-Dihydro-1-[[3-[5-[(1-Methyl-4-Piperidinyl)Methoxy]-2-PyriMidinyl]Phenyl]Methyl]-6-Oxo-3-Pyridazinyl]), golvatinib (N-(2-fluoro-4-((2-(4-(4-methylpiperazin-1-yl)piperidine-1-carboxamido)pyridin-4-yl)oxy)phenyl)-N-(4-fluorophenyl)cyclopropane-1,1-dicarboxamide), INCB28060(2-fluoro-N-methyl-4-(7-(quinolin-6-ylmethyl)imidazo[1,2-b][1,2,4]triazin-2-yl)benzamide), MK-2461(N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide), tivantinib (ARQ 197; (3R,4R)-3-(5,6-Dihydro-4H-pyrrolo[3,2,1-ij]quinolin-1-yl)-4-(1H-indol-3-yl)pyrrolidine-2,5-dione), NVP-BVU972(6-[[6-(1-Methyl-1H-pyrazol-4-yl)imidazo[1,2-b]pyridazin-3-yl]methyl]quinoline), AMG458({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833 (N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265 (N-(3-Fluoro-4-(2-(1-methyl-1H-imidazol-4-yl)thieno[3,2-b]pyridin-7-yloxy)phenylcarbamothioyl)-2-phenylacetamide), AMG-208(7-Methoxy-4-[(6-phenyl-1,2,4-triazolo[4,3-b]pyridazin-3-yl)methoxy]quinoline), BMS-754807((2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof, or any combination thereof.

The anti-c-Met antibody or an antigen-binding fragment thereof may be any antibody which specifically recognizes c-Met as an antigen and/or specifically binds to c-Met, or an antigen-binding fragment thereof. For example, the anti-c-Met antibody may be any antibody that acts on c-Met to induce intracellular internalization and degradation of c-Met, or antigen-binding fragment thereof. The anti-c-Met antibody may recognize any specific region of c-Met, e.g., a specific region in the SEMA domain, as an epitope.

Herein, unless stated otherwise, the term "anti-c-Met antibody" may be intended to cover not only an anti-c-Met antibody in a complete form (e.g., an IgG form) but also its antigen-binding fragment. The antigen-binding fragment may be at least one selected from the group consisting of scFv, (scFv)2, scFv-Fc, Fab, Fab', and F(ab')2 of an anti-c-Met antibody.

"c-Met" or "c-Met protein" refers to a receptor tyrosine kinase (RTK) which binds hepatocyte growth factor (HGF). c-Met may be derived (obtained) from any species, particularly a mammal, for instance, primates such as human c-Met (e.g., GenBank Accession No. NP_000236), monkey c-Met (e.g., Macaca mulatta, GenBank Accession No. NP_001162100), or rodents such as mouse c-Met (e.g., GenBank Accession No. NP_032617.2), rat c-Met (e.g., GenBank Accession No. NP_113705.1), and the like. The c-Met protein may comprise a polypeptide encoded by the nucleotide sequence identified as GenBank Accession No. NM_000245, a polypeptide having the amino acid sequence identified as GenBank Accession No. NP_000236 or extracellular domains thereof. The receptor tyrosine kinase c-Met participates in various mechanisms, such as cancer incidence, metastasis, migration of cancer cells, invasion of cancer cells, angiogenesis, and the like.

c-Met may comprise three portions: extracellular, transmembrane, and intracellular. The extracellular portion comprises an α-subunit and a β-subunit which are linked to each other through a disulfide bond, and comprises a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti-c-Met antibody.

The term "epitope," as used herein, refers to an antigenic determinant, a part of an antigen recognized by an antibody. In one embodiment, the epitope may be a region comprising 5 or more contiguous (consecutive on primary, secondary (two-dimensional), or tertiary (three-dimensional) structure) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide comprises at least the amino sequence of SEQ ID NO: 73 (EEPSQ) which serves as an essential element for the epitope. For example, the epitope may be a polypeptide comprising the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 is a site to which the antibody or antigen-binding fragment according to one embodiment most specifically binds.

Thus, the c-Met inhibitor may specifically bind to an epitope which has 5 to 19 contiguous amino acids selected from the amino acid sequence of SEQ ID NO: 71, comprising SEQ ID NO: 73 (EEPSQ) as an essential element. For example, the c-Met inhibitor may specifically bind to an epitope comprising the amino acid sequence of SEQ ID NO: 71, SEQ ID NO: 72, or SEQ ID NO: 73.

In one embodiment, the c-Met inhibitor or an antigen-binding fragment thereof may comprise:

at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, SEQ ID NO: 2, or an amino acid sequence comprising 8-19 consecutive amino acids within SEQ ID NO: 2 comprising amino acid residues from the $3^{rd}$ to $10^{th}$ positions of SEQ ID NO: 2; and (c) a CDR-H3 comprising the amino acid sequence of SEQ ID NO: 6, SEQ ID NO: 85, or an amino acid sequence comprising 6-13 consecutive amino acids within SEQ ID NO: 85 comprising amino acid residues from the $1^{st}$ to $6^{th}$ positions of SEQ ID NO: 85, or a heavy chain variable region comprising the at least one heavy chain complementarity determining region;

at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, SEQ ID NO: 15, SEQ ID NO: 86, or an amino acid sequence comprising 9-17 consecutive amino acids within SEQ ID NO: 89 comprising amino acid residues from the $1^{st}$ to $9^{th}$ positions of SEQ ID NO: 89, or a light chain variable region comprising the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
Xaa$_1$-Xaa$_2$-Tyr-Tyr-Met-Ser, wherein Xaa$_1$ is absent or Pro or Ser, and Xaa$_2$ is Glu or Asp, Formula II
(SEQ ID NO: 5)
Arg-Asn-Xaa$_3$-Xaa$_4$-Asn-Gly-Xaa$_5$-Thr, wherein Xaa$_3$ is Asn or Lys, Xaa$_4$ is Ala or Val, and Xaa$_5$ is Asn or Thr, Formula III
(SEQ ID NO: 6)
Asp-Asn-Trp-Leu-Xaa$_6$-Tyr, wherein Xaa$_6$ is Ser or Thr, Formula IV
(SEQ ID NO: 7)
Lys-Ser-Ser-Xaa$_7$-Ser-Leu-Leu-Ala-Xaa$_8$-Gly-Asn-Xaa$_9$-Xaa$_{10}$-Asn-Tyr-Leu-Ala wherein Xaa$_7$ is His, Arg, Gln, or Lys, Xaa$_8$ is Ser or Trp, Xaa$_9$ is His or Gln, and Xaa$_{10}$ is Lys or Asn, Formula V
(SEQ ID NO: 8)
Trp-Xaa$_{11}$-Ser-Xaa$_{12}$-Arg-Val-Xaa$_{13}$ wherein Xaa$_{11}$ is Ala or Gly, Xaa$_{12}$ is Thr or Lys, and Xaa$_{13}$ is Ser or Pro, and Formula VI
(SEQ ID NO: 9)
Xaa$_{14}$-Gln-Ser-Tyr-Ser-Xaa$_{15}$-Pro-Xaa$_{16}$-Thr wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.

In one embodiment, the CDR-H1 may comprise an amino acid sequence selected from the group consisting of SEQ ID NOS: 1, 22, 23, and 24. The CDR-H2 may comprise an amino acid sequence selected from the group consisting of SEQ ID NOS: 2, 25, and 26. The CDR-H3 may comprise an amino acid sequence selected from the group consisting of SEQ ID NOS: 3, 27, 28, and 85.

The CDR-L1 may comprise an amino acid sequence selected from the group consisting of SEQ ID NOS: 10, 29, 30, 31, 32, 33, and 106. The CDR-L2 may comprise an amino acid sequence selected from the group consisting of SEQ ID NOS: 11, 34, 35, and 36. The CDR-L3 may comprise an amino acid sequence selected from the group consisting of SEQ ID NOS: 12, 13, 14, 15, 16, 37, 86, and 89.

In another embodiment, the antibody or antigen-binding fragment may comprise a heavy chain variable region comprising a polypeptide (CDR-H1) comprising an amino acid sequence selected from the group consisting of SEQ ID NOS: 1, 22, 23, and 24, a polypeptide (CDR-H2) comprising an amino acid sequence selected from the group consisting of SEQ ID NOS: 2, 25, and 26, and a polypeptide (CDR-H3) comprising an amino acid sequence selected from the group consisting of SEQ ID NOS: 3, 27, 28, and 85; and a light chain variable region comprising a polypeptide (CDR-L1) comprising an amino acid sequence selected from the group consisting of SEQ ID NOS: 10, 29, 30, 31, 32, 33 and 106, a polypeptide (CDR-L2) comprising an amino acid sequence selected from the group consisting of SEQ ID NOS: 11, 34, 35, and 36, and a polypeptide (CDR-L3) comprising an amino acid sequence selected from the group consisting of SEQ ID NOS 12, 13, 14, 15, 16, 37, 86, and 89.

In one embodiment of the c-Met inhibitor or antigen-binding fragment, the variable region of the heavy chain comprises the amino acid sequence of SEQ ID NO: 17, 74, 87, 90, 91, 92, 93, or 94 and the variable region of the light chain comprises the amino acid sequence of SEQ ID NO: 121, 18, 19, 20, 21, 75, 88, 95, 96, 97, 98, 99, or 107.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in terms of anti-isotype response compared to animal-derived antibodies, but the variable regions still comprise animal-derived amino acids, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen, from non-human antibodies having the desired antigen specificity into a human antibody framework.

In using CDR grafting to produce humanized antibodies, choosing the human antibody framework is critical. Antibody databases, analysis of a crystal structure, and technology for molecule modeling are used to optimize the human antibody framework. However, even when the CDRs of animal-derived antibodies are grafted to the most optimized human antibody framework, in some cases, amino acids positioned in a framework of the animal-derived CDRs affecting antigen binding may be present. Therefore, in many cases, antigen binding affinity is not maintained, and thus application of additional antibody engineering technology for recovering the antigen binding affinity is necessary.

The anti c-Met antibodies may be, but are not limited to, animal antibodies (e.g., mouse-derived antibodies), chimeric antibodies (e.g., mouse-human chimeric antibodies), humanized antibodies, or human antibodies. The antibodies or antigen-binding fragments thereof may be isolated from a living body or non-naturally occurring. The antibodies or antigen-binding fragments thereof may be synthetic or recombinant. The antibody may be monoclonal.

An intact antibody comprises two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, comprising a variable region, $V_H$, that comprises amino acid sequences sufficient to provide specificity to antigens. The heavy chain may further comprise three constant regions, $C_{H1}$, $C_{H2}$, and $C_{H3}$, and a hinge. The term "light chain" refers to a full-length light chain and fragments thereof, comprising a variable region $V_L$ that comprises amino acid sequences sufficient to provide specificity to antigens. The light chain may further comprise a constant region $C_L$.

The term "complementarity determining region (CDR)" refers to an amino acid sequence found in a hyper variable region of a heavy chain or a light chain of immunoglobulin. The heavy and light chains may respectively comprise three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin comprising portions of a polypeptide comprising antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, an Fab comprises light chain and heavy chain variable regions, a light chain constant region, and a first heavy chain constant region, $C_{H1}$, and has one antigen-binding site.

The Fab' fragment is different from the Fab fragment, in that Fab' further comprises a hinge region with at least one cysteine residue at the C-terminus of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv comprises a heavy chain variable region and a light chain variable region which are linked by a non-covalent bond. Single-chain Fv generally comprises a heavy chain variable region and a light chain variable region which are linked by a covalent bond via a peptide linker or linked at the C-terminals to have a dimer structure like the two-chain Fv. The peptide linker may be the same as described above, comprising, but not limited to, those having an amino acid length of 1 to 100, 2 to 50, particularly 5 to 25, and any kinds of amino acids may be included without any restrictions.

The antigen-binding fragments may be obtained using protease or by using a genetic recombination technique. For example, the Fab fragment may be obtained by restricted cleavage of a whole antibody with papain, and the F(ab')₂ fragment may be obtained by cleavage with pepsin.

The term "hinge region," as used herein, refers to a region between CH1 and CH2 domains within the heavy chain of an antibody which functions to provide flexibility for the antigen-binding site.

When an antibody undergoes a chimerization process, the IgG1 hinge of an antigen-specific antibody of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the c-Met inhibitor or an antigen-binding fragment thereof may be modified by any combination of deletion, insertion, addition, or substitution of at least one amino acid residue on the amino acid sequence of the hinge region so that it exhibit enhanced antigen-binding efficiency. For example, the antibody may comprise a hinge region comprising the amino acid sequence of SEQ ID NO: 100(U7-HC6), 101(U6-HC7), 102(U3-HC9), 103(U6-HC8), or 104(U8-HC5), or a hinge region comprising the amino acid sequence of SEQ ID NO: 105 (non-modified human hinge). In particular, the hinge region has the amino acid sequence of SEQ ID NO: 100 or 101.

In one embodiment, the c-Met inhibitor may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The c-Met inhibitor may comprise all the antibodies defined in Korean Patent Publication No. 2011-0047698.

In the c-Met antibody or an antigen-binding fragment thereof, the portion of the light chain and the heavy chain portion besides the CDRs, the light chain variable region, and the heavy chain variable region as defined above, for example, the framework and/or the constant regions of the light chain and the heavy chain, may be from any subtype of immunoglobulin (e.g., IgA, IgD, IgE, IgG (IgG1, IgG2, IgG3, IgG4), IgM, and the like).

By way of further example, the c-Met inhibitor or the antibody fragment may comprise:

a heavy chain comprising the amino acid sequence selected from the group consisting of the amino acid sequence of SEQ ID NO: 62 (wherein the amino acid sequence from amino acid residues from the 1ˢᵗ to 17ᵗʰ positions is a signal peptide), or the amino acid sequence from the 18ᵗʰ to 462ⁿᵈ positions of SEQ ID NO: 62, the amino acid sequence of SEQ ID NO: 64 (wherein the amino acid sequence from the 1ˢᵗ to 17ᵗʰ positions is a signal peptide), the amino acid sequence from the 18ᵗʰ to 461ˢᵗ positions of SEQ ID NO: 64, the amino acid sequence of SEQ ID NO: 66 (wherein the amino acid sequence from the 1ˢᵗ to 17ᵗʰ positions is a signal peptide), and the amino acid sequence from the 18ᵗʰ to 460ᵗʰ positions of SEQ ID NO: 66; and a light chain comprising the amino acid sequence selected from the group consisting of the amino acid sequence of SEQ ID NO: 68 (wherein the amino acid sequence from the 1ˢᵗ to 20ᵗʰ positions is a signal peptide), the amino acid sequence from the 21ˢᵗ to 240ᵗʰ positions of SEQ ID NO: 68, the amino acid sequence of SEQ ID NO: 70 (wherein the amino acid sequence from the 1ˢᵗ to 20ᵗʰ positions is a signal peptide), the amino acid sequence from the 21ˢᵗ to 240ᵗʰ positions of SEQ ID NO: 70, and the amino acid sequence of SEQ ID NO: 108.

For example, the c-Met inhibitor may be selected from the group consisting of:

an antibody comprising a heavy chain comprising the amino acid sequence of SEQ ID NO: 62 or the amino acid sequence from the 18ᵗʰ to 462ⁿᵈ positions of SEQ ID NO: 62 and a light chain comprising the amino acid sequence of SEQ ID NO: 68 or the amino acid sequence from the 21ˢᵗ to 240ᵗʰ positions of SEQ ID NO: 68;

an antibody comprising a heavy chain comprising the amino acid sequence of SEQ ID NO: 64 or the amino acid sequence from the 18ᵗʰ to 461ˢᵗ positions of SEQ ID NO: 64 and a light chain comprising the amino acid sequence of SEQ ID NO: 68 or the amino acid sequence from the 21ˢᵗ to 240ᵗʰ positions of SEQ ID NO: 68;

an antibody comprising a heavy chain comprising the amino acid sequence of SEQ ID NO: 66 or the amino acid sequence from the 18ᵗʰ to 460ᵗʰ positions of SEQ ID NO: 66 and a light chain comprising the amino acid sequence of SEQ ID NO: 68 or the amino acid sequence from the 21ˢᵗ to 240ᵗʰ positions of SEQ ID NO: 68;

an antibody comprising a heavy chain comprising the amino acid sequence of SEQ ID NO: 62 or the amino acid sequence from the 18ᵗʰ to 462ⁿᵈ positions of SEQ ID NO: 62 and a light chain comprising the amino acid sequence of SEQ ID NO: 70 or the amino acid sequence from the 21ˢᵗ to 240ᵗʰ positions of SEQ ID NO: 70;

an antibody comprising a heavy chain comprising the amino acid sequence of SEQ ID NO: 64 or the amino acid sequence from the 18ᵗʰ to 461ˢᵗ positions of SEQ ID NO: 64 and a light chain comprising the amino acid sequence of SEQ ID NO: 70 or the amino acid sequence from the 21ˢᵗ to 240ᵗʰ positions of SEQ ID NO: 70;

an antibody comprising a heavy chain comprising the amino acid sequence of SEQ ID NO: 66 or the amino acid sequence from the 18ᵗʰ to 460ᵗʰ positions of SEQ ID NO: 66 and a light chain comprising the amino acid sequence of SEQ ID NO: 70 or the amino acid sequence from the 21ˢᵗ to 240ᵗʰ positions of SEQ ID NO: 70;

an antibody comprising a heavy chain comprising the amino acid sequence of SEQ ID NO: 62 or the amino acid sequence from the 18ᵗʰ to 462ⁿᵈ positions of SEQ ID NO: 62 and a light chain comprising the amino acid sequence of SEQ ID NO: 108;

an antibody comprising a heavy chain comprising the amino acid sequence of SEQ ID NO: 64 or the amino acid sequence from the 18ᵗʰ to 461ˢᵗ positions of SEQ ID NO: 64 and a light chain comprising the amino acid sequence of SEQ ID NO: 108; and an antibody comprising a heavy chain comprising the amino acid sequence of SEQ ID NO: 66 or the amino acid sequence from the 18ᵗʰ to 460ᵗʰ positions of SEQ ID NO: 66 and a light chain comprising the amino acid sequence of SEQ ID NO: 108.

According to an embodiment, the c-Met inhibitor may comprise a heavy chain comprising the amino acid sequence from the 18ᵗʰ to 460ᵗʰ positions of SEQ ID NO: 66 and a light chain comprising the sequence from the 21ˢᵗ to 240ᵗʰ positions of SEQ ID NO: 68, or a heavy chain comprising the amino acid sequence from the 18ᵗʰ to 460ᵗʰ positions of SEQ ID NO: 66 and a light chain comprising the sequence of SEQ ID NO: 108.

The polypeptide of SEQ ID NO: 70 is a light chain comprising human kappa (κ) constant region. The polypeptide with the amino acid sequence of SEQ ID NO: 68 was obtained by replacing histidine at position 62 (corresponding to position 36 according to kabat numbering) of SEQ ID NO: 70 with tyrosine. This histidine-to-tyrosine substitution may increase antibody production yield. The polypeptide with the amino acid sequence of SEQ ID NO: 108 is a polypeptide obtained by replacing serine at position 32 of SEQ ID NO: 68 (position 27e according to kabat numbering in the amino acid sequence from amino acid residues 21 to 240 of SEQ ID NO: 68; positioned within CDR-L1) with tryptophan. By such replacement, antibodies and antibody fragments comprising such sequences exhibit increased activities, such as c-Met binding affinity, c-Met degradation activity, and Akt phosphorylation inhibition.

In another embodiment, the c-Met inhibitor may comprise a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

In another embodiment, the c-Met inhibitor may be a dual inhibitor that inhibits other protein than c-Met, for example, a tumor-related protein (e.g., a growth factor (e.g., EGF, HER2, HER3, VEGF, FGF, etc.), a receptor of the growth factor (e.g., EGFR, VEGFR, FGFR, etc.), and the like), as well as c-Met, and for example, the dual inhibitor may be a bispecific antibody.

In a particular embodiment, the c-Met inhibitor may inhibit both of c-Met and EGFR. For example, the c-Met inhibitor may be an anti-c-Met/anti-EGFR bispecific antibody. The anti-c-Met/anti-EGFR bispecific antibody may comprise an anti-c-Met antibody or an antigen-binding fragment thereof; and an anti-EGFR antibody or an antigen-binding fragment thereof.

The anti-c-Met antibody or an antigen-binding fragment thereof is as described above.

The anti-EGFR antibody or an antigen-binding fragment thereof may comprise or consisting essentially of:

at least one heavy chain complementarity determining region selected from the group consisting of CDR-H1 comprising the amino acid sequence of SEQ ID NO: 109, CDR-H2 comprising the amino acid sequence of SEQ ID NO: 110, and CDR-H3 comprising the amino acid sequence of SEQ ID NO: 111, or a heavy chain variable region comprising the at least one heavy chain complementarity determining region;

at least one light chain complementarity determining region selected from the group consisting of CDR-L1 comprising the amino acid sequence of SEQ ID NO: 112, CDR-L2 comprising the amino acid sequence of SEQ ID NO: 113, and CDR-L3 comprising the amino acid sequence of SEQ ID NO: 114 or a light chain variable region comprising the at least one light chain complementarity determining region;

a combination of the at least one heavy chain complementarity determining region and the at least one light chain complementarity determining region; or a combination of the heavy chain variable region and the light chain variable region.

TABLE 1

| Heavy chain CDR | | Light chain CDR | |
|---|---|---|---|
| CDR-H1 | NYDMS (SEQ ID NO: 109) | CDR-L1 | TGSSSNIGNNDVS (SEQ ID NO: 112) |

TABLE 1-continued

| Heavy chain CDR | | Light chain CDR | |
|---|---|---|---|
| CDR-H2 | GISHSSGSKYYADSVKG (SEQ ID NO: 110) | CDR-L2 | DDNKRPS (SEQ ID NO: 113) |
| CDR-H3 | KDATPRPLKPFDY (SEQ ID NO: 111) | CDR-L3 | GSWDASLNA (SEQ ID NO: 114) |

The antigen-binding fragment may be selected from scFv, (scFv)2, scFv-Fc, Fab, Fab' and F(ab')2 of an antibody.

For example, the anti-EGFR antibody or an antigen-binding fragment thereof may comprise or consisting essentially of a heavy chain variable region comprising the amino acid sequence of SEQ ID NO: 115 or SEQ ID NO: 117, a light chain variable region comprising the amino acid sequence of SEQ ID NO: 116 or SEQ ID NO: 118, or a combination thereof.

In a particular embodiment, the anti-EGFR antibody or an antigen-binding fragment thereof may be an anti-EGFR scFv comprising or consisting essentially of a heavy chain variable region comprising the amino acid sequence of SEQ ID NO: 115 or SEQ ID NO: 117, and a light chain variable region comprising the amino acid sequence of SEQ ID NO: 116 or SEQ ID NO: 118.

<SEQ ID NO: 115: a heavy chain variable region of an anti-EGFR antibody>
EVQLLESGGGLVQPGGSLRLSCAASGFTFSNYDMSWVRQAPGKGLEWVSG

ISHSSGSKYYADSVKGRFTISRDNSKNTLYLQMNSLRAEDTAVYYCAKDA

TPRPLKPFDYWGQGTLVTVSS
(wherein the parts marked in bold type are CDR-H1, CDR-H2, and CDR-H3 in order)

<SEQ ID NO: 116: a light chain variable region of an anti-EGFR antibody>
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGGGTKLTVLG
(wherein the parts marked in bold type are CDR-L1, CDR-L2, and CDR-L3 in order)

<SEQ ID NO: 117: a heavy chain variable region of an anti-EGFR antibody>
EVQLLESGGGLVQPGGSLRLSCAASGFTFSNYDMSWVRQAPGKCLEWVSG

ISHSSGSKYYADSVKGRFTISRDNSKNTLYLQMNSLRAEDTAVYYCAKDA

TPRPLKPFDYWGQGTLVTVSS
(wherein the parts marked in bold type are CDR-H1, CDR-H2, and CDR-H3 in order)

<SEQ ID NO: 118: a light chain variable region of an anti-EGFR antibody>
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGCGTKLTVLG
(wherein the parts marked in bold type are CDR-L1, CDR-L2, and CDR-L3 in order)

In the polypeptide or an anti-EGFR scFv comprising or consisting essentially of a heavy chain variable region comprising the amino acid sequence of SEQ ID NO: 115 or SEQ ID NO: 117, and a light chain variable region comprising the amino acid sequence of SEQ ID NO: 116 or SEQ ID NO: 118, the heavy chain variable region and the light chain variable region may be linked with a linker (e.g., a peptide linker) or without a linker (e.g., via covalent bond (peptide bond)). The peptide linker may be those comprising any amino acids of 1 to 100, particularly 2 to 50, and any kinds of amino acids may be included without any restrictions. The peptide linker may comprise, for example, Gly, Asn and/or Ser residues, and also comprise neutral amino acids such as Thr and/or Ala. Amino acid sequences suitable for the peptide linker may be those known in the relevant art. Meanwhile, a length of the peptide linker may be variously determined within such a limit that the functions of the fusion protein will not be affected. For instance, the peptide linker may comprise a total of about 1 to about 100, about 2 to about 50, or about 5 to about 25 of one or more selected from the group consisting of Gly, Asn, Ser, Thr, and Ala. In one embodiment, the peptide linker may be represented as (GGGGS (SEQ ID NO 122))$_n$, wherein n is an integer of about 1 to about 10, particularly an integer of about 2 to about 5).

In the anti-EGFR antibody or an antigen-binding fragment thereof, the framework and/or light chain constant region and heavy chain constant region, may be from any subtype of immunoglobulin (e.g., IgA, IgD, IgE, IgG (IgG1, IgG2, IgG3, IgG4), IgM, and the like).

The c-Met inhibitor and/or Hsp90 inhibitor may administered together with a pharmaceutically acceptable carrier. The composition as described above may further comprise a pharmaceutically acceptable carrier in addition to a c-Met inhibitor and/or a Hsp90 inhibitor. The pharmaceutically acceptable carrier may be any one commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The composition may further comprise one or more selected from the group consisting of a lubricant, a wetting agent, a sweetener, a flavor enhancer, an emulsifying agent, a suspension agent, preservative, and the like.

The Met inhibitor and/or Hsp90 inhibitor may be administered orally or parenterally. The parenteral administration may comprise intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in the stomach. In addition, the Met inhibitor and/or Hsp90 inhibitor may be administered using an optional device that enables an active substance to be delivered to target cells.

The term "the pharmaceutically effective amount" as used in this disclosure refers to an amount at which each active ingredient can exert pharmaceutically significant effects.

For one-time administration, a pharmaceutically effective amount of a c-Met inhibitor or Hsp90 inhibitor may be prescribed in a variety of ways, depending on many factors comprising formulation methods, administration manners, ages of patients, body weight, gender, pathologic conditions, diets, administration time, administration interval, administration route, excretion rate, and reaction sensitivity. For example, the effective amount for one-time administration of a c-Met inhibitor or Hsp90 inhibitor may comprise, but not limited to, 0.001 to 100 mg/kg, or 0.02 to 10 mg/kg.

The effective amount for one-time administration may be formulated into a single formulation in a unit dosage form or formulated in suitably divided dosage forms, or it may be manufactured to be contained in a multiple dosage container. For the kit, the effective amount of a c-Met inhibitor or Hsp90 inhibitor for one-time administration (single dose) may be contained in a package container as a base unit.

The combined mixture or the pharmaceutical compositions may be formulated as a solution in oil or an aqueous medium, a suspension, a syrup, an emulsifying solution, an extract, elixir, powder, granule, a tablet or a capsule, and may further comprise a dispersing agent or a stabilizing agent in their formulation.

The c-Met inhibitor and/or Hsp90 inhibitor may be used for the prevention and/or treatment of a cancer. The cancer may be associated with overexpression and/or abnormal activation of c-Met. The cancer may be a solid cancer or a blood cancer. For example, the cancer may be but is not limited to at least one selected from the group consisting of squamous cell carcinoma, lung cancer, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophageal cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, osteosarcoma, and brain cancer. The cancer may be a primary cancer or a metastatic cancer. The cancer may be resistant to a c-Met inhibitor, for example, an anti-c-Met antibody. The cancer may be a olid cancer such as gastric cancer, lung cancer, kidney cancer, and the like, which is resistant to a c-Met inhibitor.

The cancer prevention and/or treatment may comprise suppression of cancer cell growth, migration, invasion, and/or metastasis.

The use of Hsp90 in predicting and/or monitoring an efficacy of a c-Met inhibitor (c-Met targeting drug) and in a therapy using a c-Met inhibitor may contribute to overcoming a resistance to the c-Met inhibitor. In particular, according to the disclosure, 1) the anti-cancer effect of a c-Met targeting drug can be predicted by pre-measuring the amount of Hsp90;

2) the acquisition of a resistance to a c-Met targeting drug may be identified by an increase in the amount of Hsp90;

3) when a resistance to a c-Met targeting drug is induced by increased Hsp90, the resistance can be overcome by combination administration of a c-Met targeting drug and a Hsp90 inhibitor (e.g., Hsp90 siRNA); and 4) when a resistance to a specific c-Met targeting drug is induced but there is no abnormality in activity and/or level of Hsp90, the resistance can be overcome by using another c-Met targeting drug capable of inducing a dissociation of binding between Hsp90 and c-Met.

EXAMPLES

Hereafter, the present invention will be described in detail by examples.

The following examples are intended merely to illustrate the invention and are not construed to restrict the invention.

Reference Example 1

Construction of Anti-c-Met Antibody 1.1. Production of "AbF46", a Mouse Antibody to c-Met 1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1~2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to comprise the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (database available online, operated by the National Center for Biotechnology Information (NCBI), Bethesda, Md.) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker comprising the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation

1.5.1. Selection of Target CDRs and Synthesis of Primers

The affinity maturation of huAbF46 was achieved. First, six complementary determining regions (CDRs) were defined according to Kabat numbering. The CDRs are given in Table 2, below.

TABLE 2

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y/IgG2.

Reference Example 2

Preparation of an Anti-c-Met/Anti-EGFR Bispecific Antibody 2.1. Preparation of an Anti-EGFR scFv An anti-EGFR scFv binding to EGFR was prepared by inserting a peptide linker of $(GGGGS)_3$ (SEQ ID NO: 123) between a heavy chain variable region of SEQ ID NO: 115 and a light chain variable region of SEQ ID NO: 116. In particular, the DNA sequence encoding a (GGGGS)$_3$ (SEQ ID NO: 123) linker peptide was added to the DNA sequence (SEQ ID NO: 119) encoding the heavy chain variable region (SEQ ID NO: 115) and the DNA sequence (SEQ ID NO: 120) encoding the light chain variable region (SEQ ID NO: 116) of a humanized anti-EGFR antibody using an automatic gene synthesis (Bioneer Inc.) to synthesize a DNA fragment encoding a scFv of the anti-EGFR antibody. An anti-EGFR scFv prepared from the synthesized DNA fragment was named as "anti-EGFR antibody E-2".

The amino acid sequences of the heavy chain variable region and the light chain variable region of the prepared anti-EGFR scFv, and coding nucleotide sequences thereof are summarized in Table 4, as follows (wherein the sequences marked in bold type indicate CDRs, i.e., CDR-H1, CDR-H2, and CDR-H3, or CDR-L1, CDR-L2, and CDR-L3, in sequence):

TABLE 4

|  | Heavy chain variable region of anti-EGFR antibody E-2 | Light chain variable region of anti-EGFR antibody E-2 |
| --- | --- | --- |
| Amino acid sequence | EVQLLESGGGLVQPGGSLRLSCAASG FTFSNYDMSWVRQAPGKGLEWVSGI SHSSGSKYYADSVKGRFTISRDNSKN TLYLQMNSLRAEDTAVYYCAKDATP RPLKPFDYWGQGTLVTVSS (SEQ ID NO: 115) | QSVLTQPPSASGTPGQRVTISCTGSSS NIGNNDVSWYQQLPGTAPKLLIYDDN KRPSGVPDRFSGSKSGTSASLAISGLR SEDEADYYCGSWDASLNAYVFGGGT KLTVLG (SEQ ID NO: 116) |
| Coding nucleotide sequence | GAGGTGCAGCTGTTGGAGTCTGGGG GAGGCTTGGTACAGCCTGGGGGGTC CCTGAGACTCTCCTGTGCAGCCTCTG GATTCACCTTTAGCAATTATGATAT GAGCTGGGTCCGCCAGGCTCCAGGG AAGGGGCTGGAGTGGGTCTCAGGG ATCTCTCATAGTAGTGGTAGTAAA TATTACGCTGATTCTGTAAAAGGT CGGTTCACCATCTCCAGAGACAATT CCAAGAACACGCTGTATCTGCAAAT GAACAGCCTGAGAGCCGAGGACAC GGCCGTGTATTACTGTGCGAAAGAT GCTACTCCGCGTCCGCTGAAGCCT TTCGACTACTGGGGCCAGGGTACA CTGGTCACCGTGAGCTCA (SEQ ID NO: 119) | CAGTCTGTGCTGACTCAGCCACCCT CAGCGTCTGGGACCCCCGGGCAGAG GGTCACCATCTCTTGTACTGGCTCT TCATCTAATATTGGCAATAATGAT GTCTCCTGGTACCAGCAGCTCCCAG GAACGGCCCCCAAACTCCTCATCTA TGATGATAATAAGCGGCCAAGCGG GGTCCCTGACCGATTCTCTGGCTCCA AATCTGGCACCTCAGCCTCCCTGGC CATCAGTGGGCTCCGGTCCGAGGAT GAGGCTGATTATTACTGTGGTTCTT GGGATGCTAGCCTGAATGCTTATG TCTTCGGCGGAGGCACCAAGCTGAC GGTCCTAGGC (SEQ ID NO: 120) |

A modified anti-EGFR scFv (heavy chain variable region: SEQ ID NO: 117 and light chain variable region: SEQ ID NO: 118) was prepared as described above, with the exception that the amino acid, G, at 44$^{th}$ position of the heavy chain variable region (SEQ ID NO: 115) was substituted with C, and the amino acid, G, at 100$^{th}$ position of the light chain variable region (SEQ ID NO: 116) was substituted with C. The amino acid location within the antibody complies with kabat numbering system. Such modifications (substitutions) can increase the stability of the anti-EGFR scFv.

<SEQ ID NO: 117: heavy chain variable region of modified anti-EGFR antibody E-2>
EVQLLESGGGLVQPGGSLRLSCAASGFTFSNYDMSWVRQAPGKCLEWVSG

ISHSSGSKYYADSVKGRFTISRDNSKNTLYLQMNSLRAEDTAVYYCA**KDA

TPRPLKPFDY**WGQGTLVTVSS
(wherein the sequences marked in bold type indicate CDRs, i.e., CDR-H1, CDR-H2, and CDR-H3, in sequence)

<SEQ ID NO: 118: light chain variable region of modified anti-EGFR antibody E-2>
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGCGTKLTVLG
(wherein the sequences marked in bold type indicate CDRs, i.e., CDR-L1, CDR-L2, and CDR-L3, in sequence)

The thus obtained modified anti-EGFR scFv (comprising SEQ ID NO: 117 and SEQ ID NO: 118) was used to manufacture the following bispecific antibodies.

2.2. Preparation of an Anti-c-Met/Anti-EGFR Bispecific Antibody

The modified anti-EGFR scFv (comprising SEQ ID NO: 117 and SEQ ID NO: 118) prepared in the above Reference Example 2.1 was fused at the c-terminal of Fc of the anti-c-Met antibody L3-1Y-IgG2 prepared in the above Reference Example 1. The fusion procedures are as follows.

A DNA segment having a base sequence (SEQ ID NO: 66) corresponding to the heavy chain of the anti-c-Met antibody L3-1Y-IgG2 prepared in above reference example 1 was inserted into a pcDNA™3.3-TOPO TA Cloning Kit (Cat no. 8300-01) which is included in OptiCHO™ Antibody Express Kit (Cat no. 12762-019) by Invitrogen Inc., and a DNA segment having a base sequence (SEQ ID NO: 68) corresponding to the light chain of the anti-c-Met antibody L3-1Y-IgG2 was inserted into a pOptiVEC™-TOPO TA Cloning Kit. Thereafter, the anti-EGFR scFv coding DNA prepared in Example 1 was fused at the c-terminal of Fc of L3-1Y-IgG2 inserted into pcDNA™3.3, using the coding DNA sequence of a linker peptide having 10 amino acid lengths consisting of (G4S)2, to construct vectors for the expression of bispecific antibodies.

The constructed vectors were each amplified using Qiagen Maxiprep kit (Cat no. 12662 and their temporary expressions were performed using Freestyle™ MAX 293 Expression System (invitrogen). A cell line used was 293 F cells, which were cultured in a suspension culture manner using FreeStyle™ 293 Expression Medium as a medium. One day before the temporary expression, the cells were prepared at a concentration of $5 \times 10^5$ cells/ml and after 24 hours, their temporary expression started when the number of the cells reached $1 \times 10^6$ cells/ml. Transfection was performed by a liposomal reagent method using Freestyle™ MAX reagent (invitrogen). DNA was prepared in a 15-ml tube in a ratio of heavy chain DNA:light chain DNA=3:2 and mixed with 2 ml of OptiPro™ SFM (invtrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 ml of supernatants, which were then purified using AKTA Prime (GE healthcare). The culture was flowed at a flow rate of 5 ml/min. onto the AKTA Prime installed with Protein A column (GE healthcare, 17-0405-03) to perform elution using an IgG elution buffer (Thermo Scientific, 21004). The buffer was replaced by a PBS buffer to finally obtain purified bispecific anti-c-Met/anti-EGFR antibodies.

The thus prepared anti-c-Met/anti-EGFR bispecific antibody in which the modified anti-EGFR scFv is fused at the c-terminal of L3-1Y-IgG2 was named ME22S.

Example 1

Dissociation of Hsp90-Met Binding by an Anti-c-Met Antibody

Lung cancer line H1993 (ATCC, CRL-5909) is a responsive to anti-c-Met antibody L3-1Y/IgG2 or anti-c-Met/anti-EGFR bispecific antibody ME22S, prepared in the above reference examples (i.e., L3-1Y/IgG2 or ME22S exerts an anticancer effect on H1993), whereas lung cancer line H1373 (ATCC, CRL-5866) is not responsive to L3-1Y/IgG2 or ME22S.

To confirm such responsiveness, lung cancer line H1993 (ATCC, CRL-5909) and H1373 (ATCC, CRL-5866) were incubated in RPMI1640 medium (#11875-093, Gibco) supplemented with 10% (v/v) FBS and 1% (v/v) Penicilin-Streptomycin under the conditions of 5% $CO_2$ and 37° C. To perform a cell proliferation assay, each cell line was seeded on 96 well plate at the amount of $5 \times 10^3$ cell/well, and 24 hours after, treated with each antibody (L3-1Y/IgG2 or ME22S) at the concentration of 0 nM, 0.018 nM, 0.64 nM, 3.2 nM, or 16 nM. For comparison, instead of L3-1Y/IgG2 and ME22S, a commercially available EGFR inhibitor, Erbitux (#ET509081213, Merck), was used to perform the same experiment. 72 hours after the antibody treatment, the number of the cells was measured by CellTiter Glo assay (Promega, G7573). This assay measures the number of living cells by measuring the amount of ATP which reflects a metabolism of viable cells. The CellTiter Glo assay comprises a substrate which emits luminescence when it reacts with ATP in a cell. The number of living cells can be quantified by measuring the emitted luminescence.

The obtained results are shown in FIG. 1. As shown in FIG. 1, L3-1Y/IgG2 or ME22S displays a cell proliferation inhibiting effect on H1993 cells, but does not display a cell proliferation inhibiting effect on H1373 cells.

To confirm whether or not a Met-Hsp90 binding in a L3-1Y/IgG2 or ME22S responsive H1993 cell line is dissociated when H1993 cell line was treated with L3-1Y/IgG2 or ME22S, an immunoprecipation was conducted using c-Met antibody to precipitate c-Met protein, and then, a western blotting was conducted to examine whether or not there is Hsp90 in proteins attaching to beads. In particular, to confirm whether or not the Met-Hsp90 binding is induced to be dissociated by an anti-c-Met antibody in H1993 cells, Hsp90-Met complex was isolated and purified by a co-immunoprecipitation, and quantified by an immunoblotting. H1993 cells were treated with L3-1Y/IgG2 or ME22S at the concentration of 10 nM for 30 minutes, and then, harvested. The cells was treated with a lysis buffer Complete lysis-M (Roche, 04719956001), to generate a protein extract therefrom. 500 μg of the obtained protein extract was pulled-down together with an anti-c-Met antibody conjugated A/G agarose bead (Pierce), and subjected to an immunoblotting using an anti-Hsp90 antibody (cell signaling), to identify the binding between Met and Hsp90. For comparison, the same experiment was conducted for H1373 cell line which is not responsive to L3-1Y/IgG2 or ME22S.

Figure 2:
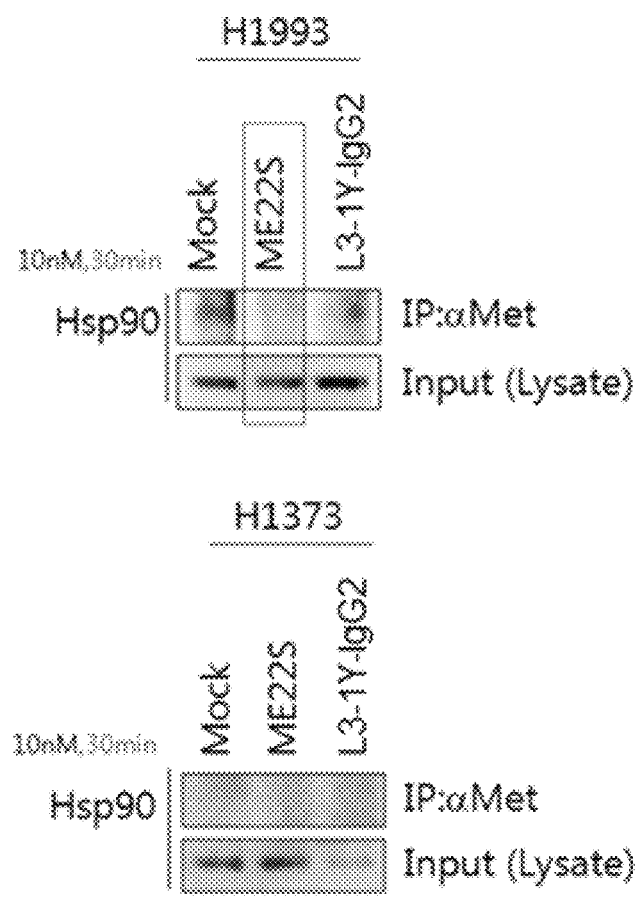
FIG. 2 displays western blotting results showing whether or not the biding between c-Met and Hsp90 is dissociated by treating anti-c-Met antibody L3-1Y/IgG2 or anti-c-Met/anti-EGFR bispecific antibody ME22S in an anti-c-Met antibody responder group, H1993 lung cancer cell line (upper panel) and an anti-c-Met antibody non-responder group, H1373 lung cancer cell line (lower panel).

The obtained results are shown in FIG. 2. As shown in FIG. 2, L3-1Y/IgG2 or ME22S induce a dissociation of the binding between Met and Hsp90 in H1993 cells. But in H1373 cells, a dissociation of the binding between Met and Hsp90 was not observed when treating L3-1Y/IgG2 or ME22S.

Example 2

Confirmation of Increase in the Amount of Hsp90 by Acquisition of a Resistance to an Anti-c-Met Antibody To measure a quantitative change of Hsp90 when a resistance to an anti-c-Met antibody is induced by repeated administration thereof, a L3-1Y/IgG2 resistant-EBC1 cell line and L3-1Y/IgG2 resistant-H1993 cell line was prepared by continued administration of L3-1Y/IgG2 to EBC1 cells (JCRB 0820) and H1993 cells (ATCC, CRL-5909). EBC1 cells (JCRB 0820) and H1993 cells (ATCC, CRL-5909) are all responsive to L3-1Y/IgG2, before the resistance is induced. The L3-1Y/IgG2 resistant-EBC1 cell line and L3-1Y/IgG2 resistant-H1993 cell line was prepared as follows: EBC1 (JCRB 0820) and H1993 (ATCC, CRL-5909) cells were treated with L3-1Y/IgG2 for 3 months with increasing the amounts. The treating amount of L3-1Y/IgG2 was increased from 1 μg/ml to 10 μg/ml until a resistance to L3-1Y/IgG2 is induced. To confirm acquisition of a resistance to L3-1Y/IgG2, the prepared cloned were treated with L3-1Y/IgG2 at various concentrations (see FIGS. 8 and 9), and 72 hours after the antibody treatment, the number of viable cells were counted by CellTiter Glo assay (Promega, G7573).

Figure 8:
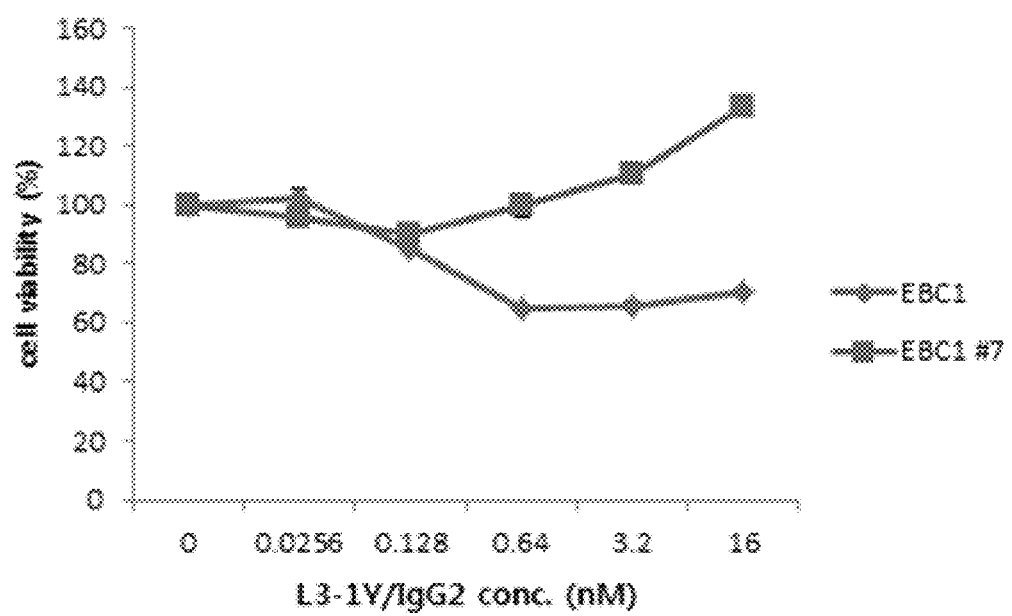
FIG. 8 is a graph displaying the degrees of cell proliferation (cell viability (%)) of anti-c-Met-antibody-resistant EBC1 cells (EBC1 #7) treated with L3-1Y/IgG2 at various concentrations.
Figure 9:
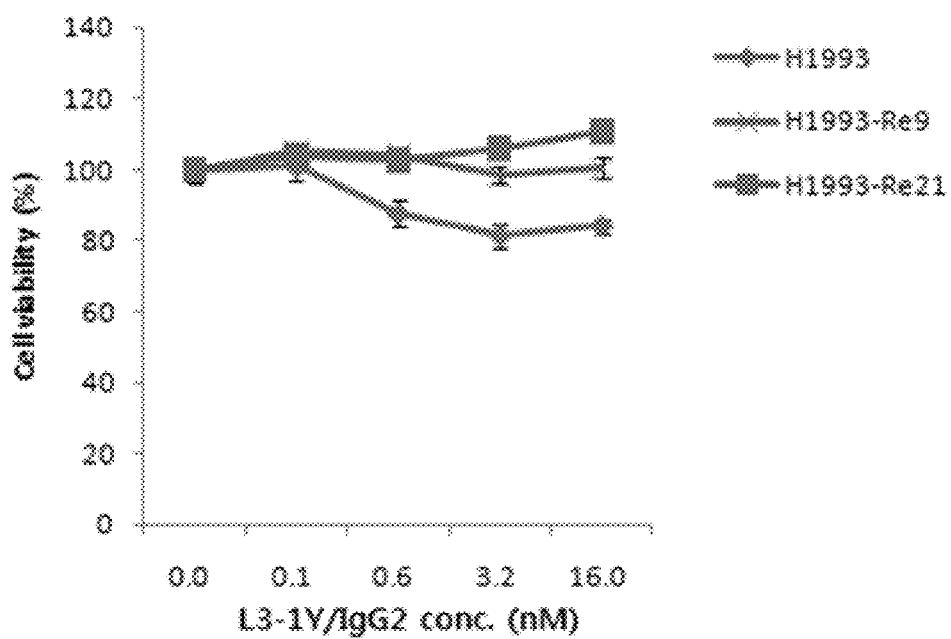
FIG. 9 is a graph displaying the degrees of cell proliferation (cell viability (%)) of anti-c-Met-antibody-resistant H1993 cells (H1993-Re9 and H1993-Re21) treated with L3-1Y/IgG2 at various concentrations.

The obtained results are shown in FIG. 8 (EBC1 cells) and FIG. 9 (H1993 cells). As shown in FIGS. 8 and 9, clones EBC1-Re7, H1993-Re9, and H1993-Re21 is confirmed to acquire a resistance to L3-1Y/IgG2. The obtained L3-1Y/IgG2-resistance acquired cell lines were named as EBC1-Re7 (EBC1-L3-1Y/IgG2 resistant cell clone #7), H1993-Re9 (H1993-L3-1Y/IgG2 resistant cell clone #9), and H1993-Re21(H1993-L3-1Y/IgG2 resistant cell clone #21), respectively.

The level of Hsp90 was measured in the L3-1Y/IgG2-resistance acquired cells. In particular, each of EBC1, EBC1-Re7, H1993, H1993-Re9, and H1993-RE #21 cell lines was seeded on 60 mm plate at the amount of $2 \times 10^5$ cells/ml. 24 hours after, the cells were lysed with a protein (using Complete lysis-M (Roche, 04719956001)) to obtain a cell lysate, and the level of Hsp90 in the cell lysate was measured by western blotting.

Figure 3:
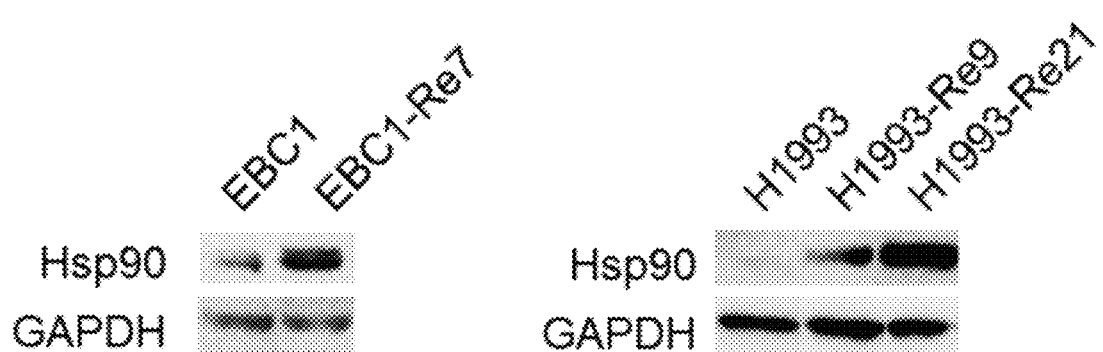
FIG. 3 displays western blotting results showing the change in Hsp90 level by acquisition of resistance to an anti-c-Met antibody (L3-1Y/IgG2).

The Hsp90 level in the L3-1Y/IgG2-resistance acquired cells was compared with that of cells with no resistance, and the obtained results are shown in FIG. 3. In FIG. 3, GAPDH (housekeeping gene) was used as a control. As shown in FIG. 3, the level of Hsp90 is considerably increased after acquiring the resistance, compared to that before acquiring the resistance, in both of EBC1 and H1993 cell lines.

Example 3

Comparison of the Levels of Hsp90 in Anti-c-Met Antibody Responsive and Non-Responsive Cells L3-1Y/IgG2-responsive cells, on which L3-1Y/IgG2 exerts the effect, comprises not only EBC1 and H1993 lung cancer cells, as used above, but also MKN45 (JCRB 0254) and Hs746T (ATCC, HTB-135) gastric cancer cell lines, and the like. L3-1Y/IgG2-non-responsive cells, on which L3-1Y/IgG2 has no effect, comprise not only H1373 lung cancer cells used above, but also HCC1806 (ATCC, CRL-2335) breast cancer cell line, Caki-1 (ATCC, HTB-46) kidney cancer cell line, SKBR3 (ATCC, HTB-30), BT474 (ATCC, HTB-20) breast cancer cell lines, HT-29 (ATCC, HTB-38), LoVo (ATCC, CCL-229), HCT116 (ATCC, CCL-247), SW620 (ATCC, CCL-227), Ls174T (ATCC, CL-188) colorectal cancer cell lines, and the like.

Figure 4:
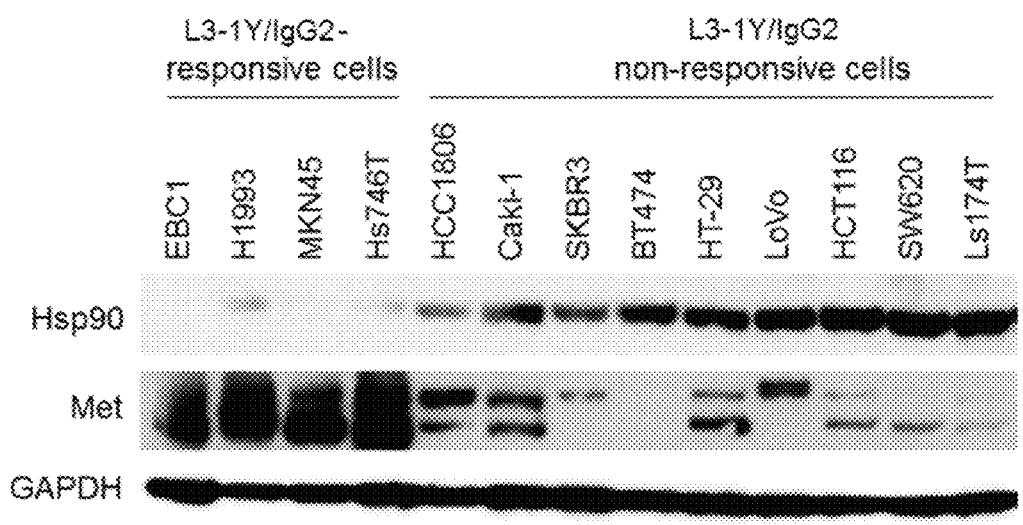
FIG. 4 displays western blotting results showing the level of Hsp90 and c-Met in anti-c-Met antibody (L3-1Y/IgG2) responsive and non-responsive cells.

Protein lysates were extracted from the cell lines at the same amount, and subjected to western blotting experiment. In particular, each of the cell lines was seeded on 60 mm plate at the amount of $2\times10^5$ cells/ml. 24 hours after, the cells were lysed with a protein (using Complete lysis-M (Roche, 04719956001)) to obtain cell lysate, and the level of Hsp90 was measured in the cell lysate by western blotting. The obtained results are shown in FIG. 4. As shown in FIG. 4, in L3-1Y/IgG2-responsive cells, the level of Hsp90 is considerably low whereas the level of c-Met is considerably high, compared to that of L3-1Y/IgG2-non-responsive cells.

Example 4

Examine an Efficacy of an Anti-c-Met Antibody or an Anti-c-Met/Anti-EGFR Bispecific Antibody when the Expression of Hsp90 is Inhibited H1373 cell line and H1993-L3-1Y/IgG2 resistant cell clone #9 were used for examine the efficacy of combination administration of an anti-c-Met antibody and Hsp90 siRNA.

5000 cells of H1373 cells (ATCC, CRL-5866) or 5000 cells of H1993-L3-1Y/IgG2 resistant cell clone #9 (see Example 2) were reverse-transfected with Hsp90 siRNA (indicated as siHsp90; 20 nM, using SMART pool of Dharmacon, catalog number: L-005186-00-0005), and seeded and cultured on 96-well plate (culture medium: 10% FBS in RPMI 1640 (GIBCO), culture temperature: 37° C.). The reverse transfection was conducted using lipofectamine RNAi max (invitrogen). The reverse transfection was conducted by pre-incubating 10~20 uM of siRNA diluted in opti-MEM (Gibco) and lipofectamine RNAi max diluted in opti-MEM (Gibco) at room temperature for 15 minutes, and mixing the pre-incubated product with 5000 cells/well of each cell line. 24 hours after, the reverse transfected cells were treated with L3-1Y/IgG2, and 72 hours after the treatment, the number of living cells was counted by Cell-Titer Glo assay (see Example 1). For comparison to Hsp90 siRNA, negative control siRNA (indicated as siNEG; using SMART pool of Dharmacon, catalog number: D-001206-14-20) was treated. L3-1Y/IgG2 was treated by 1/5 dilution starting from 10 ug/ml.

Figure 5A:
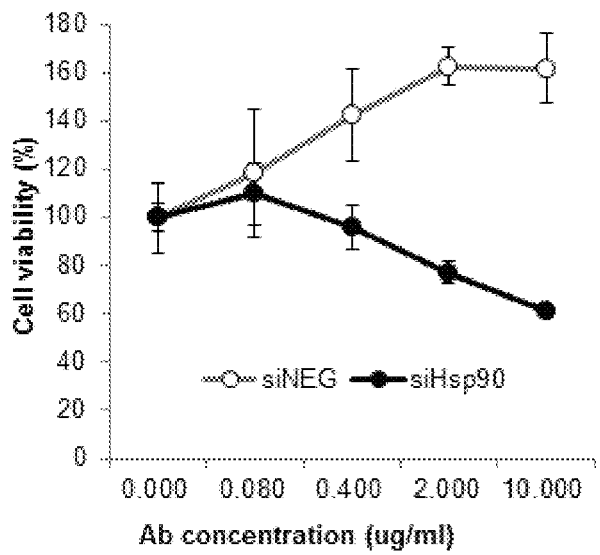
FIG. 5A contains graphs displaying the degrees of cell proliferation (cell viability (%)) of H1993 cells and H1993 Re9 cells (which are resistant to an anti-c-Met antibody) co-treated with an anti-c-Met antibody (L3-1Y/IgG2), and Hsp90 siRNA.
Figure 5A:
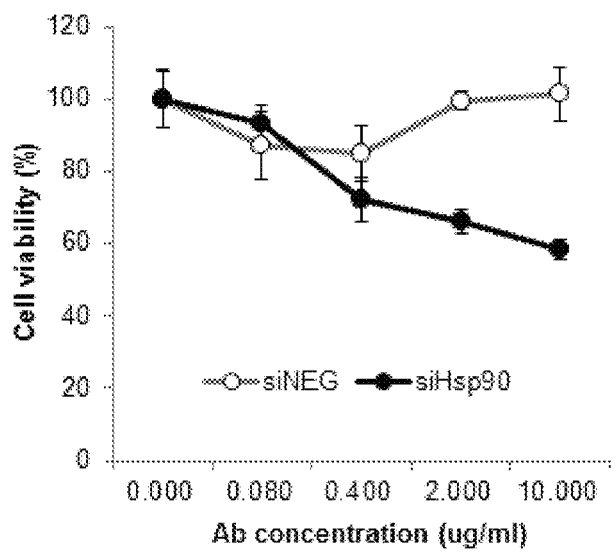

The obtained results are shown in FIG. 5A. As shown in FIG. 5A, in both of H1373 and H1993-Re9 cells, the co-administration of L3-1Y/IgG2 and Hsp90 siRNA leads to a cancer cell proliferation inhibiting effect, indicating that the anticancer effect of L3-1Y/IgG2 is expanded even to a resistance acquired cells by co-administration with Hsp90 siRNA.

Figure 5B:
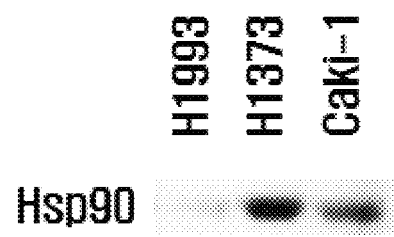
FIG. 5B displays western blotting results showing the amount of Hsp90 in H1993, H1373, and Caki-1 cells.

Each of H1993 (ATCC, CRL-5909), H1373 (ATCC, CRL-5866), and Caki-1 (ATCC, HTB-46) was seeded on 60 mm plate at the amount of $2\times10^5$ cells/ml. 24 hours after, the cells were lysed with a protein (Complete lysis-M (Roche, 04719956001)) to obtain cell lysate. The level of Hsp90 was measured in the cell lysate by western blotting, and the obtained results are shown in FIG. 5B. As shown in FIG. 5B, the expression level of Hsp90 is considerably high in L3-1Y/IgG2-non-responsive H1373 and Caki-1 cell lines, compared to that of L3-1Y/IgG2-responsive H1993 cell line.

Example 5

Examination of Efficacy of Co-Administration of an Hsp90 Inhibitor and an Anti-c-Met Antibody or an Anti-c-Met/Anti-EGFR Bispecific Antibody The efficacy of combination administration of a Hsp90 inhibitor and an anti-c-Met antibody or an anti-c-Met/anti-EGFR bispecific antibody was examined in H1993-L3-1Y/IgG2 resistant cell clone #21. 5000 cells from H1993-L3-1Y/IgG2 resistant cell clone #21 were seeded on 96-well plate, and 24 hours after, L3-1Y/IgG2 or ME22S was treated together with Hsp90 inhibitor, SNX-2112 (Selleck chemical, S2639). 72 hours after the antibody treatment, the number of living cells was counted by CellTiter Glo assay (see Example 1). The L3-1Y/IgG2 or ME22S was treated by 1/5 dilution starting from 50 nM, SNX-2112 was treated at the fixed concentration of 10 nM.

Figure 6:
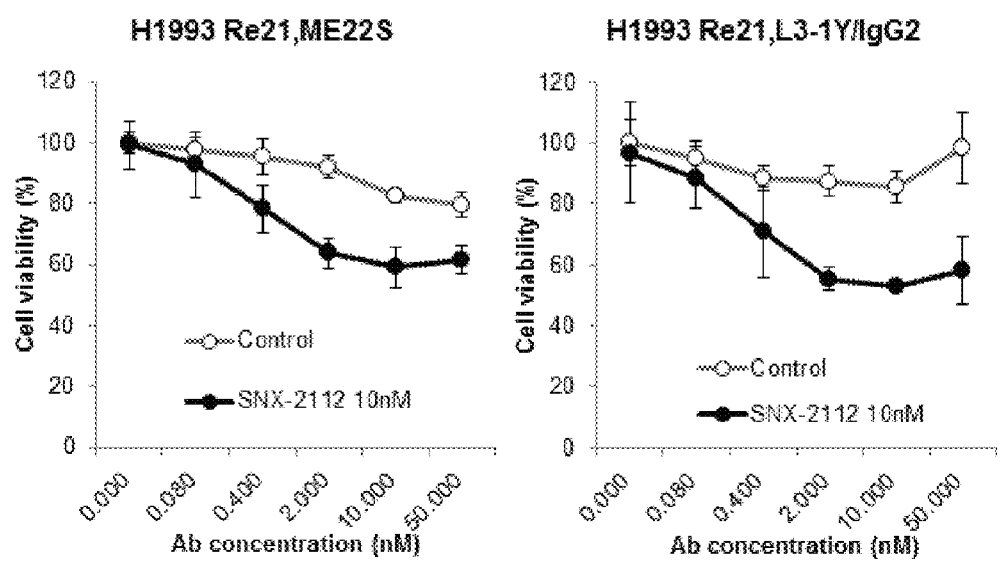
FIG. 6 contains graphs displaying the degrees of cell proliferation (cell viability (%)) of H1993 Re21 cells (which are resistant to an anti-c-Met antibody) co-treated with an anti-c-Met antibody (L3-1Y/IgG2) or an anti-c-Met/anti-EGFR bispecific antibody (ME22S), and an Hsp90 inhibitor (SNX-2112).

The obtained results are shown in FIG. 6. As shown in FIG. 6, in H1993-Re21 cells, the co-administration of L3-1Y/IgG2 or ME22 and Hsp90 inhibitor leads to a cancer cell proliferation inhibiting effect, indicating that the anticancer effect of L3-1Y/IgG2 or ME22 is expanded even to a resistance acquired cells by co-administration with Hsp90 inhibitor.

Example 6

Measurement of the Level of Hsp90 in Xenograft Mouse Model

The level of Hsp90 was measured in xenograft mouse models where lung cancer cells from patients with a variety of responsiveness to L3-1Y/IgG2 are grafted. Xenograft mouse models were prepared by grafting lung cancer cells from each patient and examined by Oncotest GmbH (Freibrug Germany). Each of Patient-driven lung cancer cell lines (non-small cell lung cancer: NSCLC), LXFA 526, LXFA 923, LXFA 1647, and LXFA 2201 was grafted into NMRI nude mice (4-6 weeks old, female; Harlan) by s.c injection, to prepared xenograft mouse models. Among them, LXFA 526 and LXFA 1647 are L3-1Y/IgG2-responsive, and LXFA 923 and LXFA 2201 are L3-1Y/IgG2-non-responsive. The preparation of the xenograft mouse models was conducted referring to Oncotest SOP "Subcutaneous implantation". The number of mice per each group was 5.

In particular, a tissue sample from the xenograft mouse model was lysed with a lysis buffer to extract proteins using Complete lysis-M (Roche, 04719956001), and the level of Hsp90 and c-Met was measured by western blotting.

Figure 7:
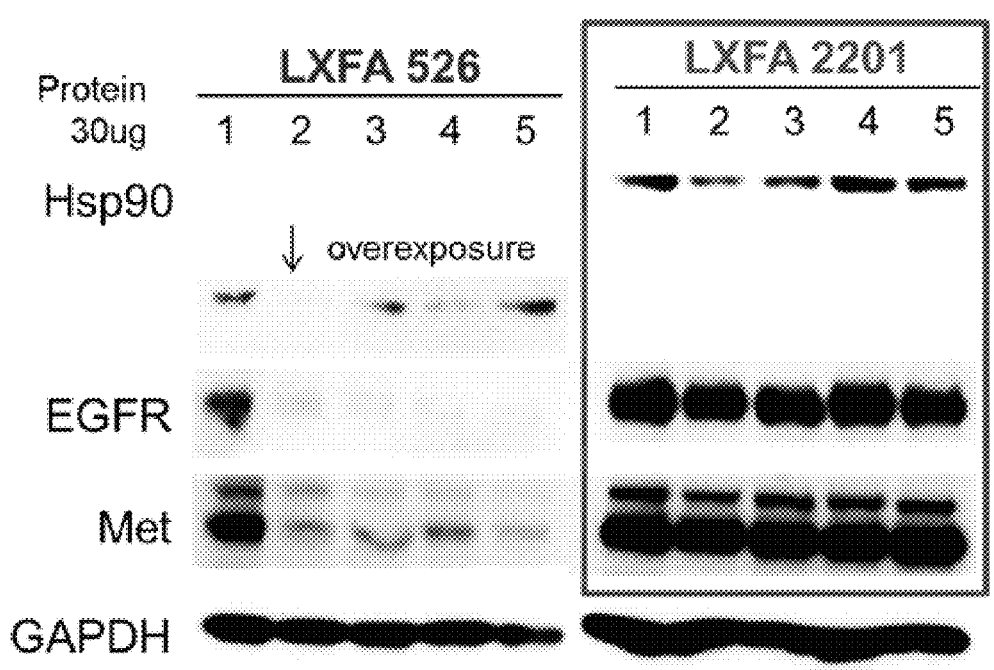
FIG. 7 displays western blotting results showing the level of Hsp90 in mouse xenograft models who were grafted with patient-derived lung cancer (non-small cell lung cancer) cells, LXFA 526 (which is L3-1Y/IgG2 responsive) and LXFA 2201 (which is L3-1Y/IgG2 non-responsive).

The obtained results are shown in FIG. 7. As shown in FIG. 7, it is confirmed that, the high level of Hsp90 contributes to L3-1Y/IgG2-non responsiveness of LXFA 2201, in spite of higher level of c-Met than that of L3-1Y/IgG2-responsive LXFA 526.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A method of selecting a subject for application of a c-Met inhibitor, the method comprising:
   measuring Hsp90 alpha protein level and/or Hsp90 alpha gene expression level,
   detecting a mutation of Hsp90 alpha and/or an Hsp90 alpha coding gene;
   or a combination thereof,
   in a biological sample from a patient with lung cancer, and
   selecting the patient for application of the c-Met inhibitor, when
   the Hsp90 alpha protein level or the Hsp90 alpha gene expression level in the biological sample from the patient is lower than that of a reference sample in which the c-Met inhibitor has no effect, and/or the mutation of Hsp90 alpha or the Hsp90 alpha coding gene is identified in the biological sample,
   wherein the mutation of Hsp90 alpha is C598A, I128T, or a combination thereof, of human Hsp90 alpha, and the Hsp90 alpha coding gene is a gene encoding a human Hsp90 alpha comprising the mutation of C598A, I128T, or a combination thereof,
   the method further comprising administering the c-Met inhibitor to the patient if
   (a) the Hsp90 alpha protein level or the Hsp90 alpha gene expression level in the biological sample from the patient is lower than that of a reference sample in which the c-Met inhibitor has no effect, and/or
   (b) the mutation of Hsp90 alpha or the Hsp90 alpha coding gene is identified in the biological sample.

2. The method of claim 1, further comprising:
   measuring c-Met protein level and/or c-Met gene expression level.

3. The method of claim 1, wherein the c-Met inhibitor is at least one selected from the group consisting of an anti-c-Met antibody or an antigen-binding fragment thereof, crizotinib, cabozantinib, foretinib, PHA-665752, SU11274, SGX-523, PF-04217903, EMD 1214063, golvatinib, INCB28060, MK-2461, tivantinib, NVP-BVU972, AMG458, BMS 794833, BMS 777607, MGCD-265, AMG-208, JNJ-38877605, and pharmaceutically acceptable salts thereof.

4. The method of claim 3, wherein the anti-c-Met antibody or an antigen-binding fragment thereof recognizes or binds to a polypeptide comprising 5 to 19 contiguous amino acid residues within the amino acid sequence of SEQ ID NO: 71 and wherein the polypeptide comprises at least the amino sequence of SEQ ID NO: 73.

5. The method of claim 1, wherein
   the c-Met inhibitor is an anti-c-Met/anti-EGFR bispecific antibody comprising an anti-c-Met antibody or an antigen-binding fragment thereof and an anti-EGFR antibody or an antigen-binding fragment thereof, wherein
   the anti-c-Met antibody or an antigen-binding fragment thereof recognizes or binds to a polypeptide comprising 5 to 19 contiguous amino acid residues within the amino acid sequence of SEQ ID NO: 71 and wherein the polypeptide comprises at least the amino sequence of SEQ ID NO: 73;
   and
   the anti-EGFR antibody or an antigen-binding fragment thereof comprises:
   a CDR-H1 comprising the amino acid sequence of SEQ ID NO: 109, a CDR-H2 comprising the amino acid sequence of SEQ ID NO: 110, a CDR-H3 comprising the amino acid sequence of SEQ ID NO: 111,
   a CDR-L1 comprising the amino acid sequence of SEQ ID NO: 112, a CDR-L2 comprising the amino acid sequence of SEQ ID NO: 113, and a CDR-L3 comprising the amino acid sequence of SEQ ID NO: 114.

6. The method of claim 4, wherein the anti-c-Met antibody or an antigen-binding fragment thereof comprises:
   (1) a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 13,
   (2) a CDR-H1 of SEQ ID NO: 1, a CDR-H2 of SEQ ID NO: 2, a CDR-H3 of SEQ ID NO: 3, a CDR-L1 of SEQ ID NO: 106, a CDR-L2 of SEQ ID NO: 11, and a CDR-L3 of SEQ ID NO: 13,
   (3) a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 12,
   (4) a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 14,
   (5) a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 15, or
   (6) a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 16.

* * * * *